(12) United States Patent
Shimada et al.

(10) Patent No.: US 10,231,683 B2
(45) Date of Patent: Mar. 19, 2019

(54) BREAST IMAGING APPARATUS

(71) Applicant: CANON KABUSHIKI KAISHA, Tokyo (JP)

(72) Inventors: Tetsuo Shimada, Hachioji (JP); Osamu Tsujii, Kawasaki (JP); Hiroshi Komatsu, Yokohama (JP); Sakiko Yamaguchi, Tokyo (JP); Nobuhiro Takeuchi, Yokohama (JP); Takahiro Noguchi, Tokyo (JP); Hitomi Ogasawara, Kawasaki (JP); Chifuyu Inagaki, Tokyo (JP); Yoshinori Hirano, Kashiwa (JP)

(73) Assignee: Canon Kabushiki Kaisha, Tokyo (JP)

( * ) Notice: Subject to any disclaimer, the term of this patent is extended or adjusted under 35 U.S.C. 154(b) by 220 days.

(21) Appl. No.: 15/195,627

(22) Filed: Jun. 28, 2016

(65) Prior Publication Data

US 2017/0000436 A1 Jan. 5, 2017

(30) Foreign Application Priority Data

Jun. 30, 2015 (JP) ................................. 2015-132185

(51) Int. Cl.
*A61B 6/00* (2006.01)
*A61B 6/03* (2006.01)
*A61B 6/04* (2006.01)
*A61B 6/10* (2006.01)

(52) U.S. Cl.
CPC ............ *A61B 6/4435* (2013.01); *A61B 6/032* (2013.01); *A61B 6/4417* (2013.01); *A61B 6/502* (2013.01); *A61B 6/035* (2013.01); *A61B 6/04* (2013.01); *A61B 6/0414* (2013.01); *A61B 6/107* (2013.01); *A61B 6/461* (2013.01); *A61B 6/467* (2013.01)

(58) Field of Classification Search
CPC ........... A61B 6/032; A61B 6/04; A61B 6/107; A61B 6/4435; A61B 6/502; A61B 6/035; A61B 6/0414; A61B 6/4417
See application file for complete search history.

(56) References Cited

U.S. PATENT DOCUMENTS 4,961,208 A * 10/1990 Okada .................... A61B 6/04
378/18
2001/0055362 A1* 12/2001 Takanashi ............. A61B 6/035
378/15

(Continued)

FOREIGN PATENT DOCUMENTS

JP 2013538668 A 10/2013

*Primary Examiner* — Chih-Cheng Kao
(74) *Attorney, Agent, or Firm* — Canon U.S.A., Inc. IP Division

(57) ABSTRACT

A breast imaging apparatus includes a gantry which includes a radiation generation unit configured to generate radiation and a radiation detection unit configured to detect radiation generated by the radiation generation unit, the radiation generation unit and the radiation detection unit being capable of rotating facing each other, wherein the gantry is provided with a front cover configured to protect a subject from the radiation generation unit and the radiation detection unit which rotate during CT imaging, and the front cover has an opening in which the breast of the subject is inserted, and a breast holding portion configured to hold the breast of the subject inserted in the opening.

13 Claims, 14 Drawing Sheets

(56) References Cited

U.S. PATENT DOCUMENTS

| | | | |
|---|---|---|---|
| 2006/0050844 A1* | 3/2006 | Galkin | A61B 6/0414 378/37 |
| 2006/0262898 A1* | 11/2006 | Partain | A61B 6/032 378/37 |
| 2007/0092059 A1* | 4/2007 | Wayne Eberhard | A61B 6/502 378/37 |
| 2013/0259193 A1* | 10/2013 | Packard | A61B 6/025 378/37 |
| 2014/0048730 A1* | 2/2014 | Niedzielski | A61B 6/107 250/519.1 |
| 2014/0077102 A1* | 3/2014 | Bowlsbey | A63B 69/16 250/492.1 |
| 2014/0119494 A1* | 5/2014 | Youn | A61B 6/032 378/4 |
| 2015/0265232 A1* | 9/2015 | Kodaira | A61B 6/032 378/15 |

* cited by examiner

BREAST IMAGING APPARATUS

BACKGROUND OF THE INVENTION

Field of the Invention

The present invention relates to a breast imaging apparatus for imaging breasts using radiation.

Description of the Related Art

A breast imaging apparatus that images the breast using a radiation generation unit which generates radiation and a radiation detection unit which detects radiation has been proposed.

Further, mammographic imaging and CT imaging are performed with the same breast imaging apparatus (for example, see PCT Japanese Translation Patent Publication No. 2013-538668).

In the breast imaging apparatus disclosed in PCT Japanese Translation Patent Publication No. 2013-538668, the breast of a subject is fixed between two plates during the CT imaging. Therefore, imaging the breast while holding the breast suitably is difficult. The present invention provides a breast imaging apparatus capable of performing CT imaging while holding the breast of a subject suitably.

SUMMARY OF THE INVENTION

According to an aspect of the present invention, a breast imaging apparatus, includes a gantry which includes a radiation generation unit configured to generate radiation and a radiation detection unit configured to detect radiation generated by the radiation generation unit, the radiation generation unit and the radiation detection unit being capable of rotating facing each other, wherein the gantry is provided with a front cover configured to protect a subject from the radiation generation unit and the radiation detection unit which rotate during CT imaging, and the front cover has an opening in which the breast of the subject is inserted and a breast holding portion configured to hold the breast of the subject inserted in the opening.

Further features of the present invention will become apparent from the following description of exemplary embodiments with reference to the attached drawings.

DESCRIPTION OF THE EMBODIMENTS

Figure 1:
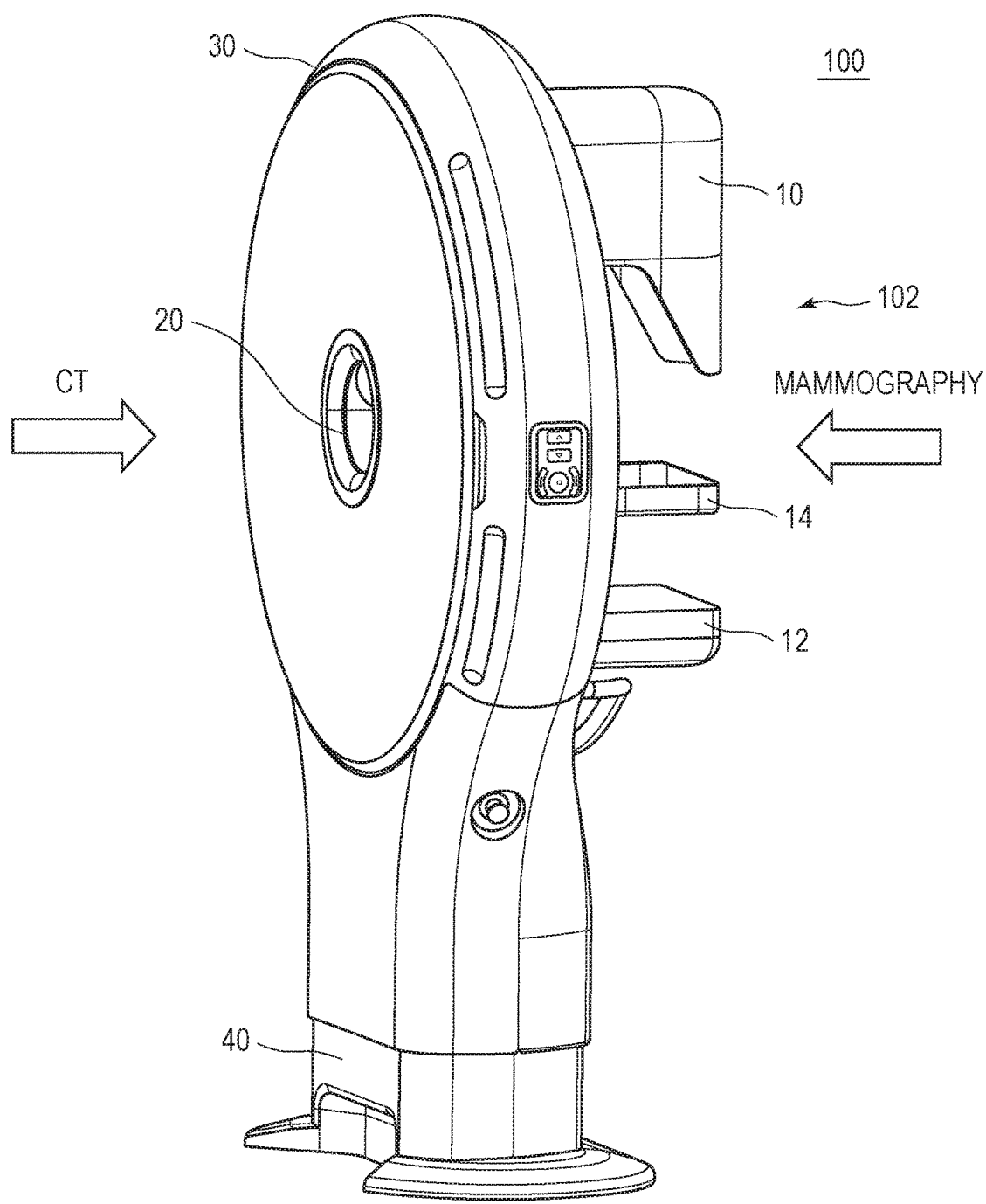
FIG. 1 is a diagram illustrating an exterior of a breast imaging apparatus of the present invention.

FIG. 1 illustrates an exterior of a breast imaging apparatus 100. The breast imaging apparatus 100 may be used for the mammographic imaging and CT imaging. A subject is at a standing position during the mammographic imaging and CT imaging. In the standing position, the subject stands on the floor with the feet placed on the floor. The breast imaging apparatus 100 is a breast imaging apparatus for the standing position.

The breast imaging apparatus 100 includes a radiation generation unit 10 for generating radiation, and a radiation detection unit 12 for detecting radiation generated by the radiation generation unit 10. The breast imaging apparatus 100 may rotate the radiation generation unit 10 and the radiation detection unit 12 facing each other. An image capturing unit 102 consists mainly of the radiation generation unit 10 and the radiation detection unit 12.

A part to be imaged (the breast) of the subject is imaged while being compressed by a compression plate 14 from a first side in the breast imaging apparatus 100. Here, the part to be imaged (the breast) is inserted between the compression plate 14 and the radiation detection unit 12. A grid (not illustrated) may be provided on an upper surface of the radiation detection unit 12, and the part to be imaged (the breast) of the subject may be imaged while being inserted between the compression plate 14 and the grid. That is, the breast imaging apparatus 100 has a first image capturing unit which is in a mammographic imaging mode. The part to be imaged (the breast) of the subject is imaged with the radiation generation unit 10 and the radiation detection unit 12 rotating in a state in which the part to be image is inserted between the radiation generation unit 10 and the radiation detection unit 12 from a second side opposite to the first side in the breast imaging apparatus 100. That is, the breast imaging apparatus 100 has a second image capturing unit which is in a CT imaging mode.

The breast imaging apparatus 100 is provided with a gantry 30 which supports the radiation generation unit 10 and the radiation detection unit 12 rotatably, and a support leg portion 40 which supports the gantry 30 with respect to the floor. That is, the gantry 30 supports the imaging unit 102 rotatably.

During the mammographic imaging, the part to be imaged (the breast) of the subject is imaged with the part to be imaged inserted between the compression plate 14 and the radiation detection unit 12 from the first side (the right side of FIG. 1) in the breast imaging apparatus 100. The compression plate 14 is formed by a transparent, radiation-transmissive material. Specifically, the breast of the subject may be inserted between the compression plate 14 and the radiation detection unit 12 by moving the compression plate 14 up and down. Radiation is generated by the radiation generation unit 10 with the breast of the subject inserted between the compression plate 14 and the radiation detection unit 12. The radiation detection unit 12 detects radiation which has penetrated the breast of the subject, whereby the breast of the subject is imaged. The breast imaging apparatus 100 may generate a mammogram image based on the imaged radiation data.

During the CT imaging, the part to be imaged (the breast) of the subject is inserted between the radiation generation unit 10 and the radiation detection unit 12 from the second side opposite to the first side (the left side in FIG. 1) in the breast imaging apparatus 100. In this state, the part to be imaged (the breast) of the subject is imaged with the radiation generation unit 10 and the radiation detection unit 12 rotated by a rotating frame 38. An opening 20 through which the breast of the subject is inserted is formed in the gantry 30 of the breast imaging apparatus 100. The breast of the subject is inserted in the opening 20 and is imaged with the radiation generation unit 10 and the radiation detection unit 12 rotated by the rotating frame 38. The radiation generation unit 10 generates radiation while the radiation generation unit 10 and the radiation detection unit 12 are rotated by the rotating frame 38. The radiation detection unit 12 detects radiation which has penetrated the breast of the subject, whereby the breast of the subject is imaged. The breast imaging apparatus 100 may generate a CT image by reconstructing imaged radiation data.

The first side in the breast imaging apparatus 100 is the mammographic imaging side and the second side in the breast imaging apparatus 100 is the CT imaging side. A line which horizontally connects the first side (the mammographic imaging side) and the second side (the CT imaging side) is substantially parallel to a rotational shaft of the rotating frame 38. A line which horizontally connects the first side (the mammographic imaging side) and the second side (the CT imaging side) crosses perpendicularly a plane of the substantially plate-shaped gantry 30 or a plane of a front cover 26.

The first side (the mammographic imaging side) and the second side (the CT imaging side) in the breast imaging apparatus 100 are partitioned by the substantially plate-shaped gantry 30, the front cover 26, and the imaging unit 102 of the breast imaging apparatus 100.

Figure 2:
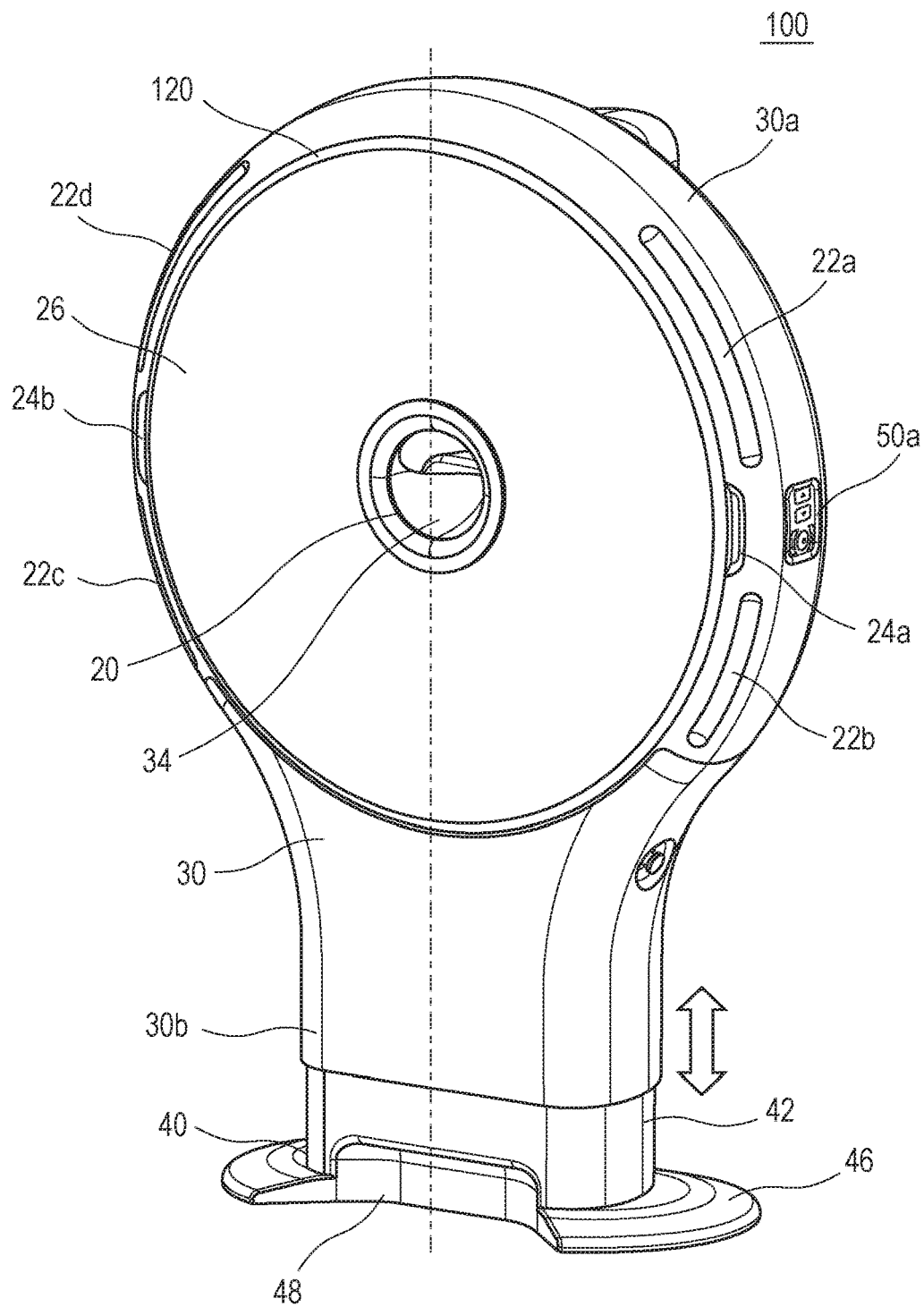
FIG. 2 is a diagram illustrating an exterior of the breast imaging apparatus of the present invention seen from a CT imaging side.
Figure 3:
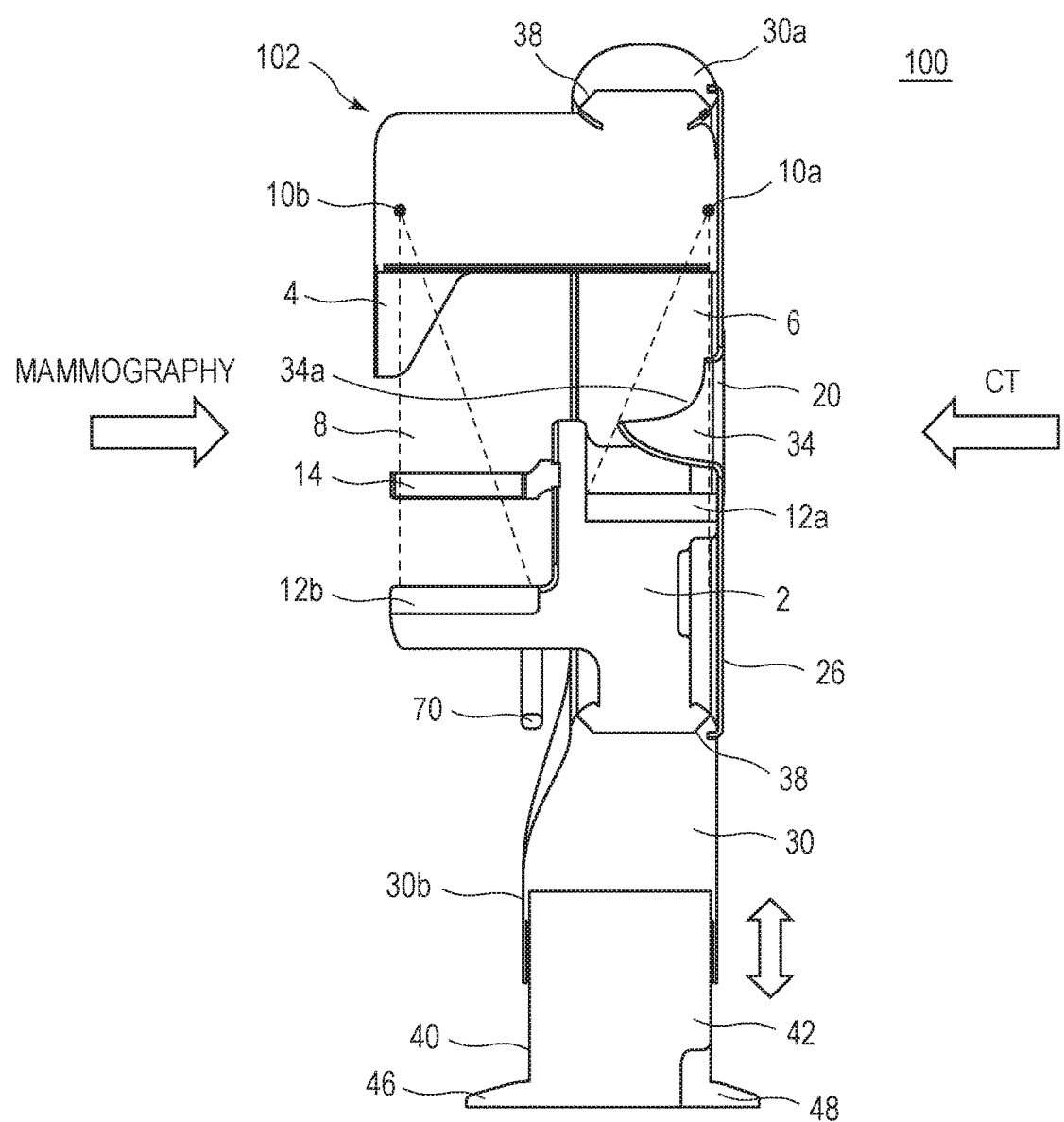
FIG. 3 is cross-sectional view of the breast imaging apparatus of the present invention.
Figure 4:
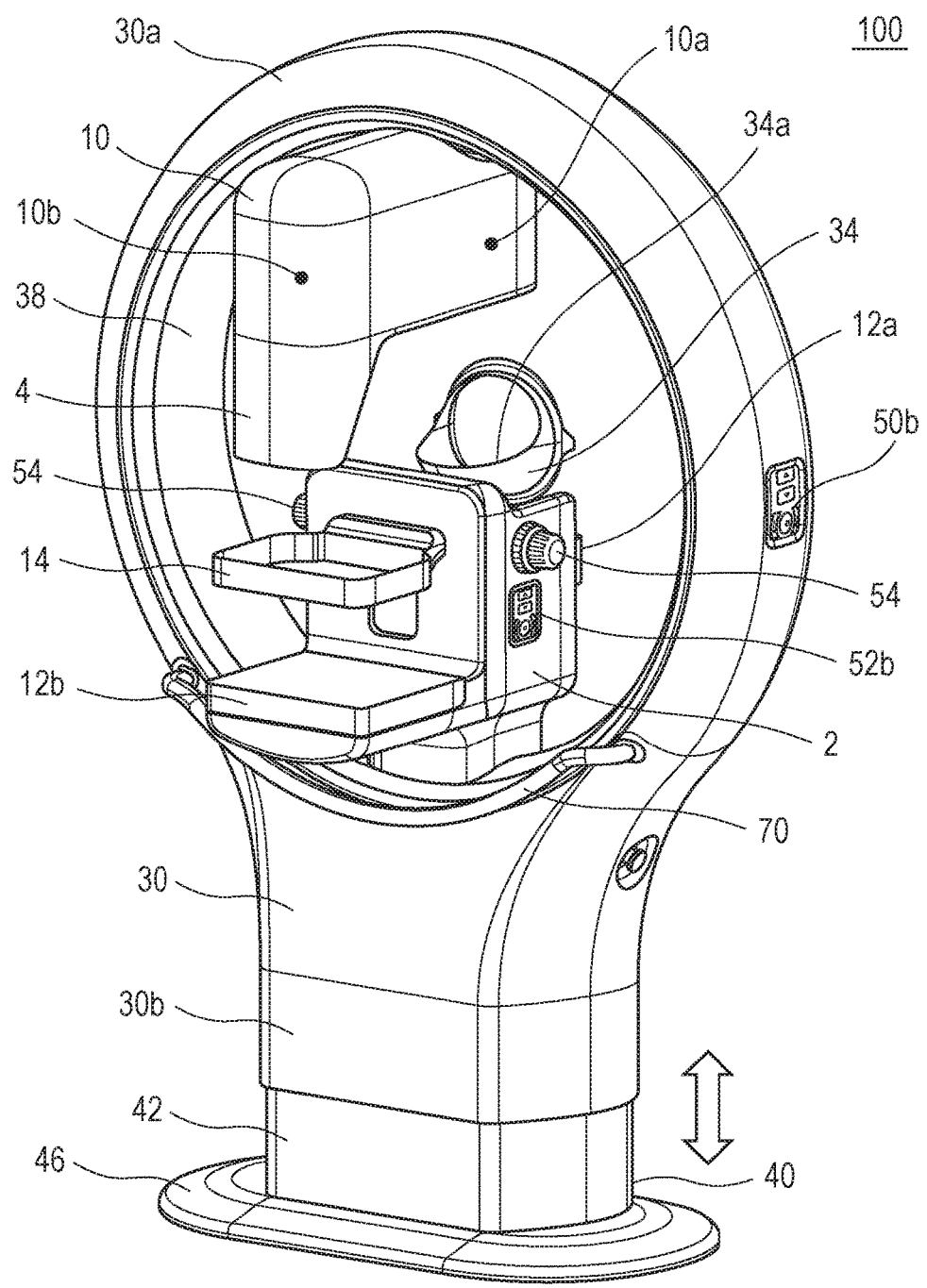
FIG. 4 is a diagram illustrating an exterior of the breast imaging apparatus of the present invention seen from a mammographic imaging side.

The breast imaging apparatus 100 is described in detail with reference to FIGS. 2 to 4. FIG. 2 is a diagram illustrating an exterior of the breast imaging apparatus 100 seen from the CT imaging side. FIG. 3 is a cross-sectional view of the breast imaging apparatus 100. The cross-sectional view of the breast imaging apparatus 100 is taken along a center line (a dash-dot line) extending in the vertical direction of the breast imaging apparatus 100 of FIG. 2. FIG. 4 is a diagram illustrating an exterior of the breast imaging apparatus 100 seen from the mammographic imaging side.

As illustrated in FIG. 2, the front cover 26 for protecting the subject from the radiation generation unit 10 and the radiation detection unit 12 which rotate during the CT imaging is provided in the gantry 30 on the CT imaging side. The front cover 26 has the opening 20 in which the breast of the subject of the CT imaging is inserted. A plurality of gripping portions 22a, 22b, 22c, and 22d to be gripped by the subject during the CT imaging are provided in the gantry 30 on the CT imaging side. A plurality of gripping portions 22a, 22b, 22c, and 22d are formed as recesses. A recessed portion 48 in which the subject places the feet during the CT imaging is provided in the support leg portion 40 on the CT imaging side.

As illustrated in FIG. 4, the compression plate 14 which compresses the breast of the subject during the mammographic imaging is provided in the gantry 30 on the mammographic imaging side. A protection plate 4 for protecting the subject from unnecessary exposure is provided in the gantry 30 on the mammographic imaging side. A gripping portion 70 to be gripped by the subject during the mammographic imaging is provided in the gantry 30 on the mammographic imaging side. The gripping portion 70 is formed as a projection. No recessed portion 48 in which the subject places the feet during the mammographic imaging is provided in the support leg portion 40 on the mammographic imaging side.

Figure 5:
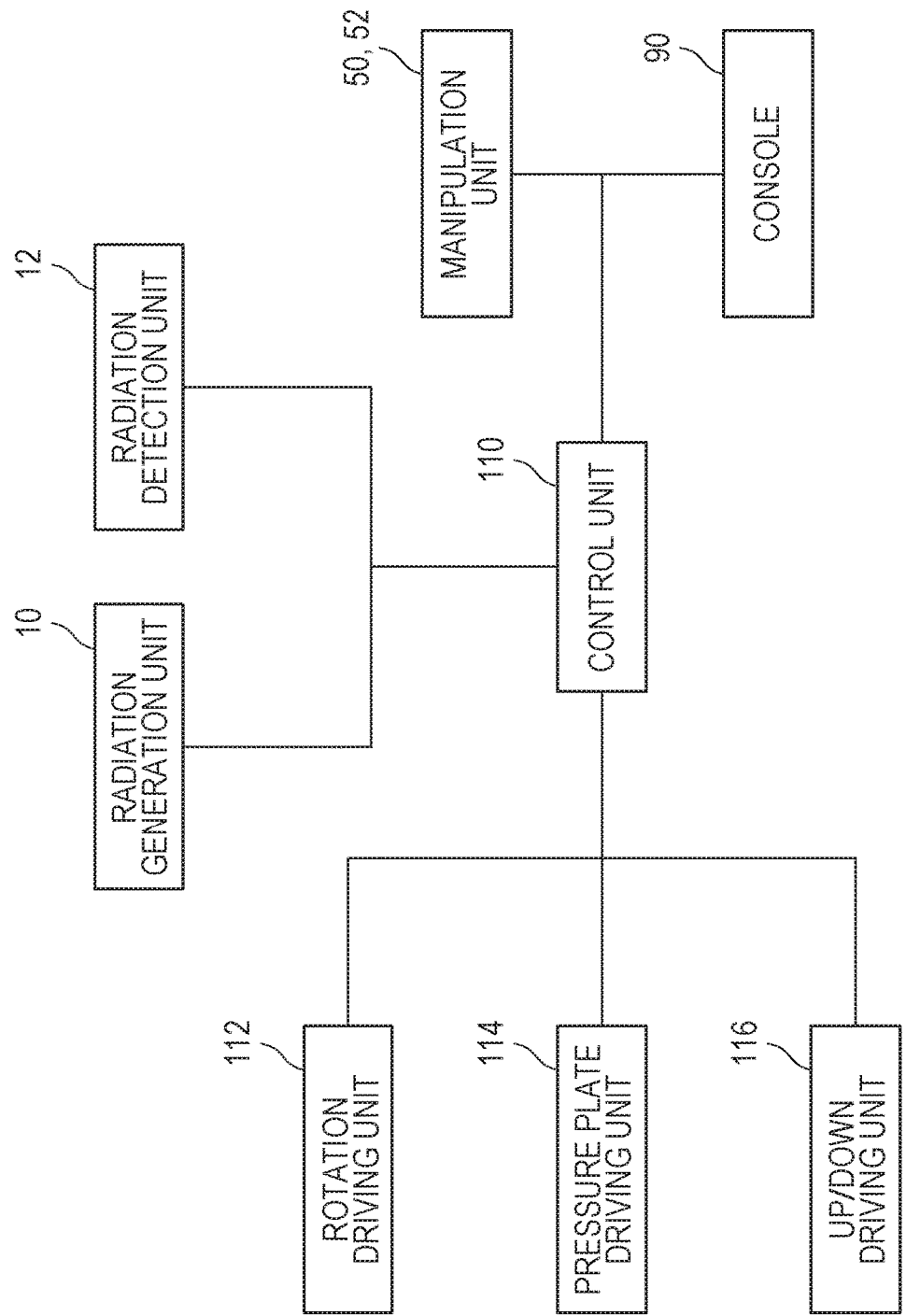
FIG. 5 is a diagram illustrating a configuration of the breast imaging apparatus of the present invention.

FIG. 5 is a configuration diagram of the breast imaging apparatus 100. The breast imaging apparatus 100 is provided with a rotation driving unit 112 which rotates the radiation generation unit 10 and the radiation detection unit 12 facing each other. The breast imaging apparatus 100 is provided with a compression plate driving unit 114 which moves the compression plate 14 up and down, and an up/down driving unit 116 which moves the gantry 30 up and down with respect to the support leg portion 40.

The breast imaging apparatus 100 is provided with a control unit 110 which controls the radiation generation unit 10, the radiation detection unit 12, the rotation driving unit 112, the compression plate driving unit 114, and the up/down driving unit 116. The breast imaging apparatus 100 is provided with manipulation units 50 and 52 and a console 90 from which instructions are transmitted to the control unit 110. A manipulation unit 50 for manipulating the breast imaging apparatus 100 is provided in the gantry 30, and the manipulation unit 52 having the same function as that of the manipulation unit 50 is provided in a support base 2 supporting the radiation detection unit 12. The console 90 is provided outside an imaging room.

A display unit for displaying any one of subject information, height information of a radiation detection unit 12b, dose information of a radiation generation unit 10b, and the compression information (N) by the compression plate 14 may be provided in the support base 2.

Although not illustrated, the radiation generation unit 10 is provided with an electron emission source for emitting electrons, and a target. The electrons emitted from the electron emission source are directed toward the target due to a potential difference between a cathode and an anode. The target is a member which generates radiation by electronic collisions. Radiation generated by the target is formed into a cone beam shape and is emitted to the outside. The control unit 110 may control imaging conditions of the radiation generation unit 10.

The radiation detection unit 12 detects radiation which has penetrated the subject by a photoelectric conversion element, and outputs as electrical signals. The radiation detection unit 12 is constituted by, for example, a conversion panel for detecting radiation penetrated the subject, an electricity storage portion, an interface (I/F) for outputting information converted from radiation into electrical signals, and the like. The electrical signals are output to the control unit 110 via the interface (I/F).

Gantry

As illustrated in FIGS. 2 to 4, the gantry 30 has the ring-shaped rotating frame 38 for rotating the radiation generation unit 10 and the radiation detection unit 12 facing each other, and a ring-shaped fixed frame 30a for supporting the rotating frame 38 rotatably. The fixed frame 30a is ring-shaped and may support a part of the rotating frame 38 rotatably. The gantry 30 has an elongated cylindrical portion 30b connected to the fixed frame 30a. The rotating frame 38 and the fixed frame 30a may also be called a rotating portion which rotates the radiation generation unit 10 and the radiation detection unit 12. The fixed frame 30a and the elongated cylindrical portion 30b are formed integrally with each other. The fixed frame 30a is located above the elongated cylindrical portion 30b. The elongated cylindrical portion 30b is connected to the support leg portion 40 which supports the gantry 30 with respect to the floor.

The gantry 30 is provided upright in the vertical direction so that the subject may be imaged at the standing position. The rotational shaft of the rotating portion (the rotating frame 38 of the gantry 30) which rotates the radiation generation unit 10 and the radiation detection unit 12 is horizontally positioned.

The elongated cylindrical portion 30b covers the periphery of an elongated cylindrical portion 42 of the support leg portion 40. That is, the elongated cylindrical portion 42 of the support leg portion 40 is disposed inside the elongated cylindrical portion 30b of the gantry 30. The elongated cylindrical portion 42 of the support leg portion 40 fits into the elongated cylindrical portion 30b of the gantry 30.

The breast imaging apparatus 100 is provided with the up/down driving unit 116 which moves the elongated cylindrical portion 30b up and down with respect to the support leg portion 40. That is, the breast imaging apparatus 100 is provided with the up/down driving unit 116 which moves the gantry 30 up and down.

Figure 6:
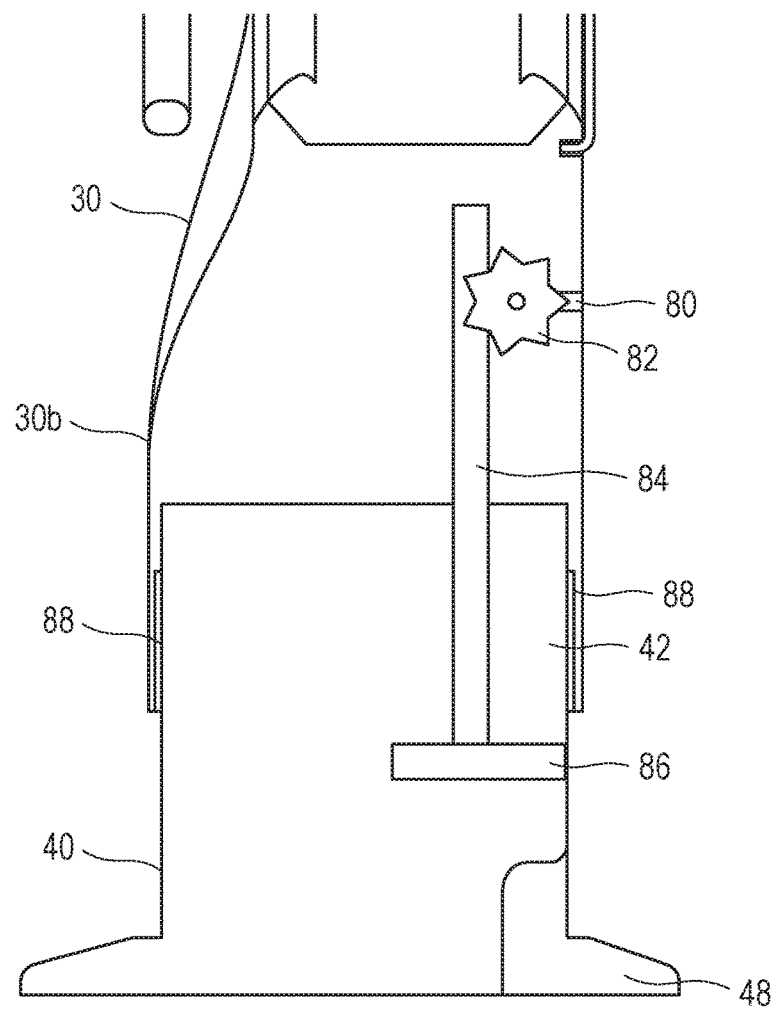
FIG. 6 is a diagram illustrating a configuration of an up/down driving unit of the breast imaging apparatus of the present invention.

FIG. 6 is a diagram illustrating a configuration of the up/down driving unit 116 which moves the gantry 30 up and down. The gantry 30 and the support leg portion 40 are hollow. Inside the gantry 30, a round gear 82, and a support portion 80 which supports the round gear 82 rotatably are provided. The rotational shaft of the round gear 82 is parallel to the horizontal plane. The support portion 80 supports the round gear 82 so that the rotational shaft of the round gear 82 is parallel to the horizontal plane. Although not illustrated, a driving unit (a motor) for rotating the round gear 82 is provided inside the gantry 30.

A plate-shaped bar member 84 and a support portion 86 which supports the bar member 84 are provided inside the support leg portion 40. The plate-shaped bar member 84 is provided along the longitudinal direction (the up-down direction) of the support leg portion 40. The longitudinal direction of the support leg portion 40 crosses perpendicularly the horizontal plane. The plate-shaped bar member 84 is provided to extend across the inside of the support leg portion 40 and the inside of the gantry 30. The breast imaging apparatus 100 may be provided with a shock absorbing material 88 which fills a gap between the elongated cylindrical portion 30b of the gantry 30 and the elongated cylindrical portion 42 of the support leg portion 40 and reduces rattling between the elongated cylindrical portion 30b of the gantry 30 and the elongated cylindrical portion 42 of the support leg portion 40.

The round gear 82 and the bar member 84 mesh with each other. The bar member 84 may be moved up and down when rotational force is applied to the round gear 82 by the driving unit (the motor). Specifically, when the round gear 82 is rotated counterclockwise by the driving unit (the motor), the bar member 84 may be moved downward with respect to the gantry 30. When the round gear 82 is rotated counterclockwise, a distance between the support portion 80 supporting the round gear 82 and the support portion 86 supporting the bar member 84 increases. In this manner, the gantry 30 may be moved upward when the round gear 82 in the up/down driving unit 116 is rotated counterclockwise.

The bar member 84 may be moved upward with respect to the gantry 30 when the rotating the round gear 82 is rotated clockwise by the driving unit (the motor). When the round gear 82 is rotated clockwise, a distance between the support portion 80 supporting the round gear 82 and the support portion 86 supporting the bar member 84 decreases. In this manner, the gantry 30 may be moved downward when the round gear 82 in the up/down driving unit 116 is rotated clockwise.

As described above, the breast imaging apparatus 100 may move the gantry 30 up and down by the up/down driving unit 116. By moving the gantry 30 up and down, the height of the opening 20 may be adjusted in accordance with the height of the breast of the subject.

The height at which the breast of the subject is inserted between the compression plate 14 and the radiation detection unit 12 may be adjusted when the gantry 30 is moved up and down in accordance with the height of the breast of the subject.

Although the up/down driving unit 116 employs a rack and pinion gears as an example, other forms, such as a combination of a cam follower and a guide rail, may also be used.

Radiation Generation Unit and Radiation Detection Unit

The breast imaging apparatus 100 is provided with the radiation generation unit 10 which generates radiation, and radiation detection unit 12 which detects the radiation generated by the radiation generation unit 10. The breast imaging apparatus 100 may rotate the radiation generation unit 10 and the radiation detection unit 12 facing each other.

The radiation generation unit 10 and the radiation detection unit 12 are provided in the rotating frame 38 which is rotated with respect to the fixed frame 30a of the gantry 30. As illustrated in FIG. 3, the breast imaging apparatus 100 is provided with a radiation generation unit 10a and a radiation detection unit 12a for the CT imaging, and the radiation generation unit 10b and the radiation detection unit 12b for the mammographic imaging. The gantry 30 is provided with the radiation generation unit 10a and the radiation detection unit 12a for the CT imaging, and the radiation generation unit 10b and the radiation detection unit 12b for the mammographic imaging. That is, the breast imaging apparatus 100 is provided with two sets of radiation generation units and radiation detection units for the CT imaging and for the mammographic imaging.

The gantry 30 has the ring-shaped rotating frame 38 for rotating the radiation generation unit 10a and the radiation detection unit 12a for the CT imaging facing each other, and the radiation generation unit 10b and the radiation detection unit 12b for the mammographic imaging facing each other.

Specifically, the radiation generation unit 10a and the radiation detection unit 12a are provided in the rotating frame 38 for the CT imaging. The radiation detection unit 12a is provided in the rotating frame 38 via the support base 2 which supports the radiation detection unit 12a.

The radiation generation unit 10b and the radiation detection unit 12b are provided in the rotating frame 38 for the mammographic imaging. The radiation detection unit 12b is provided in the rotating frame 38 via the support base 2.

The rotating frame 38 is connected to the fixed frame 30a of the gantry 30 via a bearing which has a bearing structure. The fixed frame 30a is an unmoving, stable frame. The rotating frame 38 may be rotated by the rotation driving unit 112. The rotation driving unit 112 is provided inside the gantry 30 so that the rotational shaft of the rotating frame 38 is horizontal.

The compression plate 14 is provided in the support base 2 to be moved up and down. A rotary knob 54 for moving the compression plate 14 up and down is provided in the support base 2. The breast of the subject may be compressed between the compression plate 14 and the radiation detection unit 12b when the rotary knob 54 is rotated to move the compression plate 14 down.

In this manner, the support base 2 is provided in the rotating frame 38, and the support base 2 supports the radiation detection unit 12a, the radiation detection unit 12b, and the compression plate 14. The radiation detection unit 12a and the radiation detection unit 12b may be rotated when the rotating frame 38 is rotated together with the support base 2 by the rotation driving unit 112. The radiation generation unit 10a and the radiation generation unit 10b may be rotated when the rotating frame 38 is rotated by the rotation driving unit 112.

As illustrated in FIG. 3, the radiation generation unit 10a and the radiation generation unit 10b are provided at substantially the same height. The radiation detection unit 12a is provided at a position higher than the radiation detection unit 12b.

That is, the radiation generation unit 10a and the radiation generation unit 10b are disposed at the same position (the same distance) with respect to the rotational shaft of the rotating portion (the rotating frame 38).

The radiation detection unit 12a and the radiation detection unit 12b are disposed with the radiation detection unit 12b located outside the radiation detection unit 12a with respect to the rotational shaft of the rotating portion (the rotating frame 38).

The distance between the radiation generation unit 10a and the radiation detection unit 12a used during the CT imaging is shorter than the distance between the radiation generation unit 10b and the radiation detection unit 12b used during the mammographic imaging.

When performing mammographic imaging, the breast of the subject is compressed between the compression plate 14 and the radiation detection unit 12b. Due to the compression, the thickness of the breast of the subject is reduced and the breast becomes substantially plate-shaped. Therefore, it is required to increase a radiation irradiating area to provide a field of view (FOV). For this reason, the radiation detection unit 12b used during the mammographic imaging is provided at a position lower than the radiation detection unit 12a used during the CT imaging.

An irradiation field 8 is an irradiation field by the radiation generation unit 10b for the mammographic imaging. The radiation generation unit 10b and the radiation detection unit 12b are disposed so that the irradiation field 8 from the radiation generation unit 10b includes the compression plate 14. The irradiation field 8 has a pyramid shape (a cone beam shape) with a focal point of the radiation generation unit 10b as a peak. As illustrated in FIG. 3, one side edge (the left side) of the irradiation field 8 extends vertically, and the other side edge (the right side) of the irradiation field 8 extends obliquely. In order to image the periphery of the breast of the subject (an axilla), the irradiation field 8 of the radiation generation unit 10b is set so that an end portion of the irradiation field 8 (an irradiation field end portion, an irradiation field end surface) on the side of the subject of the mammographic imaging (the left side) is in the vertical direction.

Regarding the CT imaging, the radiation generation unit 10a and the radiation detection unit 12a are disposed so that the size of the rotating frame 38 and the entire size of the breast imaging apparatus 100 (the gantry 30) is reduced. Specifically, the radiation generation unit 10a and the radiation detection unit 12a are disposed as close as possible to each other. The radiation detection unit 12a is disposed directly below the breast holding portion 34. The radiation detection unit 12a is disposed at a position where the radiation detection unit 12a is not in contact with the breast holding portion 34 even when the radiation detection unit 12a is rotated by the rotating frame 38.

An irradiation field 6 is generated by the radiation generation unit 10a for the CT imaging. The breast of the subject of the CT imaging is held on the breast holding portion 34 and is not compressed. The radiation generation unit 10a and the radiation detection unit 12a are disposed so that the irradiation field 6 from the radiation generation unit 10a includes an end portion of the breast holding portion 34.

The irradiation field 6 has a pyramid shape (a cone beam shape) with a focal point of the radiation generation unit 10a as a peak. As illustrated in FIG. 3, one side edge (the right side) of the irradiation field 6 extends vertically, and the other side edge (the left side) of the irradiation field 6 extends obliquely. In order to image the periphery of the breast of the subject (the axilla), the irradiation field 6 of the radiation generation unit 10a is set so that an end portion of the irradiation field 6 (an irradiation field end portion, an irradiation field end surface) on the side of the subject of the CT imaging (the right side) is in the vertical direction.

In this manner, the end portion (the irradiation field end portion, the irradiation field end surface) of the irradiation field 8 on the side of the subject of the mammographic imaging (the left side) is set to be in the vertical direction, and the end portion (the irradiation field end portion, the irradiation field end surface) of the irradiation field 6 on the side of the subject of the CT imaging (the right side) is set to be in the vertical direction. Breast cancer can metastasize to the periphery of the breast (the axilla). The irradiation field 6 of the radiation generation unit 10a for the CT imaging and the irradiation field 8 of the radiation generation unit 10b for the mammographic imaging are set to image the periphery of the breast of the subject (the axilla).

During the CT imaging, in order to provide the FOV, the radiation generation unit 10a for the CT imaging may be provided at a position higher than the radiation generation unit 10b for the mammographic imaging. During the CT imaging, the radiation generation unit 10a and the radiation detection unit 12a are rotated with the radiation generation unit 10a generating radiation from the focal point.

As described above, the breast imaging apparatus 100 of the present invention is provided with the first radiation generation unit 10a which generates radiation and the second radiation generation unit 10b which generates radiation. The breast imaging apparatus 100 is provided with the first radiation detection unit 12a which detects radiation generated by the first radiation generation unit 10a and the second radiation detection unit 12b which detects radiation generated by the second radiation detection unit 10b.

The part to be imaged of the subject is imaged by the second radiation generation unit 10b and the second radiation detection unit 12b with the part to be imaged compressed between the compression plate 14 and the second radiation detection unit 12b from the first side in the breast imaging apparatus 100. The part to be imaged of the subject is imaged with the first radiation detection unit 10a and the first radiation detection unit 12a rotating in a state in which the part to be imaged is inserted between the first radiation detection unit 10a and the first radiation detection unit 12a from the second side opposite to the first side in the breast imaging apparatus 100.

That is, the breast imaging apparatus 100 is provided with two sets of radiation generation units and radiation detection units for the CT imaging and for the mammographic imaging. Therefore, field of views (FOV) suitable for each of the breast of the subject of the CT imaging and the breast of the subject of the mammographic imaging are provided.

Rotating Frame

The breast imaging apparatus 100 is provided with the rotation driving unit 112 which drives the radiation generation unit 10 and the radiation detection unit 12 to rotate via the rotating frame 38. The radiation generation unit 10 has the radiation generation unit 10b for the mammographic imaging and the radiation generation unit 10a for the CT imaging inside.

FIG. 4 illustrates a form for performing mammographic imaging of a caraniocaudal view (CC) in the breast imaging apparatus 100. The position of the rotating frame 38 is determined so that the radiation generation unit 10b, the compression plate 14, and the radiation detection unit 12b are arranged vertically.

When the rotary knob 54 is rotated, the compression plate 14 is moved to adjust the distance between the compression plate 14 and the radiation detection unit 12b. The breast of the subject may be compressed as the compression plate 14 is moved. During the mammographic imaging of the CC view illustrated in FIG. 4, the breast disposed between the compression plate 14 and the radiation detection unit 12b is compressed and imaged with radiation between the compression plate 14 and the radiation detection unit 12b.

The rotation driving unit 112 is provided inside the fixed frame 30a. The rotating frame 38 is rotatably connected to the rotation driving unit 112 via a connecting member (for example, a belt). A bearing is set in a gap between the fixed frame 30a and the rotating frame 38. When driven by the rotation driving unit 112, the rotating frame 38 is rotated with respect to the fixed frame 30a.

Figure 7:
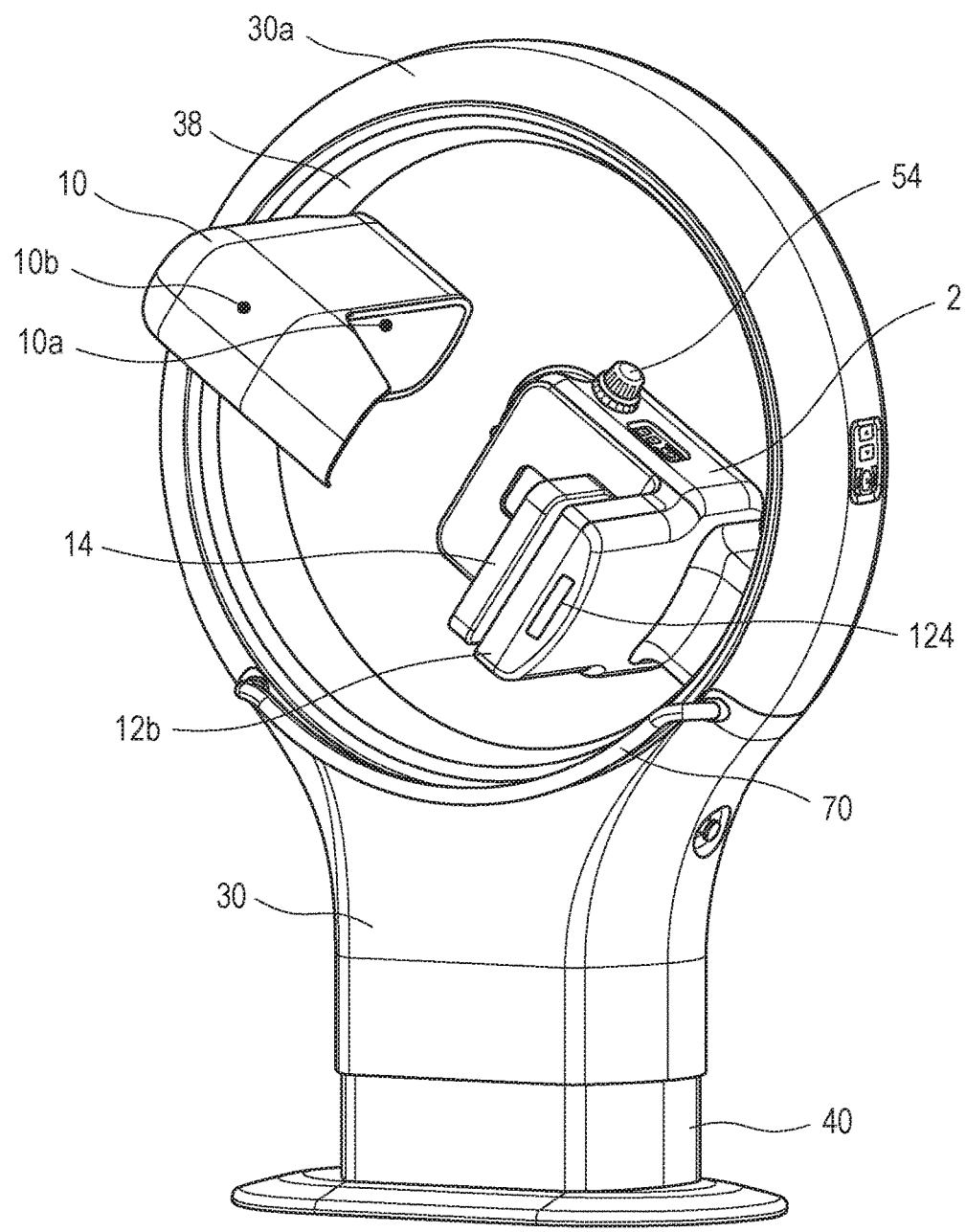
FIG. 7 is a diagram illustrating a rotated form by a rotation driving unit of the breast imaging apparatus of the present invention.

FIG. 7 is a diagram illustrating a rotated form of the radiation generation unit 10b and the radiation detection unit 12b rotated by the rotation driving unit 112 of the breast imaging apparatus 100. During the mammographic imaging of a mediolateral oblique (MLO) view in the breast imaging apparatus 100, as illustrated in FIG. 7, the rotating frame 38 is rotated by a predetermined angle (for example, about 65 degrees) from the state illustrated in FIG. 4 and stopped. The stationary state of the rotating frame 38 may be kept by a servomechanism or a brake system. In the mammographic imaging of the MLO view illustrated in FIG. 7, the breast disposed between the compression plate 14 and the radiation detection unit 12b is compressed and imaged with radiation between the compression plate 14 and the radiation detection unit 12b.

During the CT imaging, the rotating frame 38 is rotated with respect to the fixed frame 30a when driven by the rotation driving unit 112. Specifically, the rotating frame 38 is rotated at least 180 degrees. When the rotating frame 38 is rotating, the radiation generation unit 10a generates radiation and the radiation detection unit 12a detects radiation. The radiation detection unit 12 detects radiation which has penetrated the breast of the subject, whereby CT imaging of the breast of the subject is performed. The breast imaging apparatus 100 may generate a CT image by reconstructing imaged radiation data.

Front Cover

The front cover 26 is detachably attached to the gantry 30 of the breast imaging apparatus 100. That is, the front cover 26 is detachably attached to the ring-shaped fixed frame 30a. Specifically, the front cover 26 is fixed to the fixed frame 30a with a projecting portion of the front cover 26 fitting into a frame (a groove portion) of the fixed frame 30a.

Figure 8B:
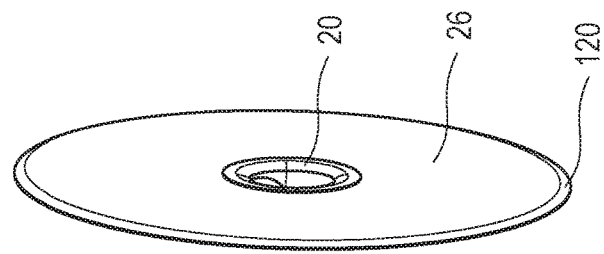
FIGS. 8A and 8B are diagrams illustrating the breast imaging apparatus of the present invention with a front cover detached from a gantry.
Figure 8A:
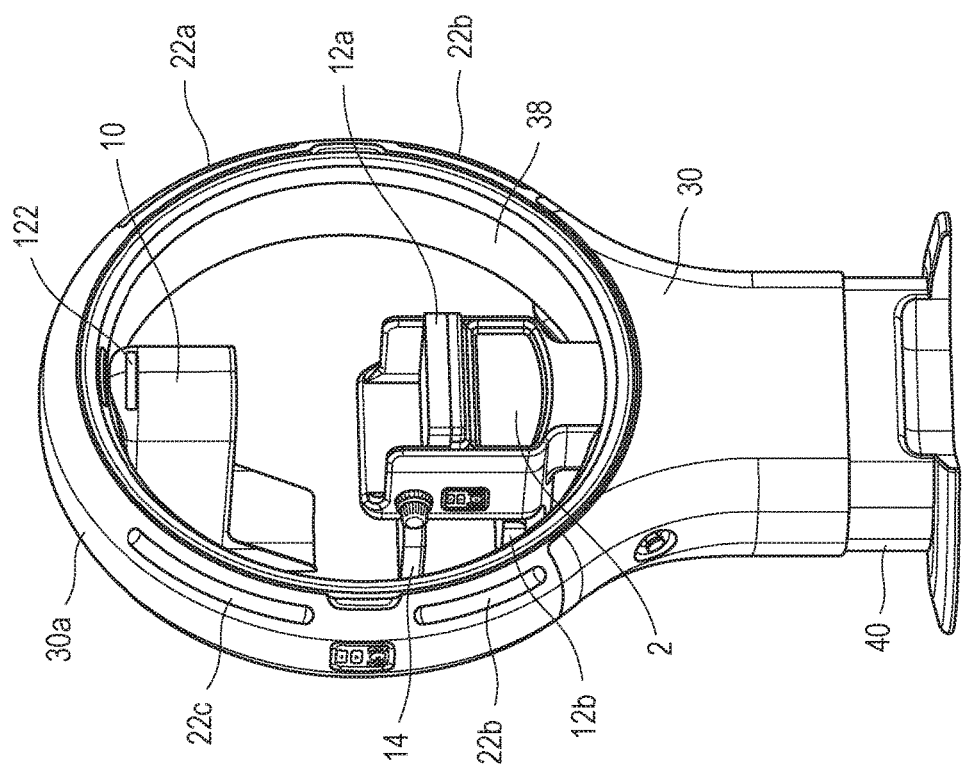

FIG. 2 illustrates a form in which the front cover 26 is attached to the gantry 30 of the breast imaging apparatus 100. FIGS. 8A and 8B are diagrams illustrating the breast imaging apparatus 100 of the present invention with the front cover 26 detached from the gantry 30.

As illustrated in FIGS. 8A and 8B, when the front cover 26 is detached from the gantry 30, an operator may access the breast of the subject of the mammographic imaging from the CT imaging side via a hollow portion of the rotating frame 38. During the mammographic imaging, position adjustment and compression adjustment may be performed about the breast disposed between the radiation detection unit 12b and the compression plate 14 of the breast imaging apparatus 100.

Since the fixed frame 30a of the gantry 30 is ring-shaped, the front cover 26 is also ring-shaped. The front cover 26 is only required to be fixed to a member that is not moved with respect to the rotation of the radiation generation unit 10 and the radiation detection unit 12.

The front cover 26 has the opening 20 through which the breast of the subject is inserted. Specifically, as illustrated in FIG. 2, the round opening 20 through which the breast of the subject is inserted is provided at the center of the front cover 26.

The front cover 26 is formed by a radiation-shielding member. Scattered radiation does not penetrate the front cover 26 during the CT imaging or the mammographic imaging. That is, the scattered radiation does not reach the CT imaging side. The front cover 26 is formed by a translucent member. Since the front cover 26 is translucent, the positions of the radiation generation unit 10 and the radiation detection unit 12 may be checked from the CT imaging side when the front cover 26 is attached to the gantry 30.

As illustrated in FIGS. 3 and 4, a breast holding portion 34 as a holding stand for holding the breast inserted from the opening 20 is provided in the front cover 26. The breast holding portion 34 is formed by a transparent, radiation-transmissive member. The breast holding portion 34 is formed along the periphery of the opening 20 of the front cover 26. The breast holding portion 34 is formed to project on the imaging unit 102 side from the opening 20 of the front cover 26.

The breast holding portion 34 is hollow and curved to conform to the shape of the breast. A part (a lower part) of the breast holding portion 34 is bowl-shaped, and a part (an upper part) of the breast holding portion 34 is open. The breast holding portion 34 has an opening 34a through which the operator accesses the breast from the mammographic imaging side.

The breast holding portion 34 holds the lower side of the breast. The breast holding portion 34 may hold the breast while keeping the shape of the breast. The breast holding portion 34 does not compress the breast.

As illustrated in FIG. 4, since a part (an upper part) of the breast holding portion 34 is open, the operator of the CT imaging may access the breast of the subject from the mammographic imaging side. That is, the operator may access, from the mammographic imaging side, the breast of the subject held by the breast holding portion 34.

The breast holding portion 34 is detachably attached to the front cover 26. Various sizes of breast holding portions 34 may be prepared. That is, the operator may prepare a plurality of breast holding portions 34. The operator may change the breast holding portions 34 depending on, for example, the size of the breast of the subject.

The front cover 26 and the breast holding portion 34 fixed to the gantry 30 separates the radiation generation unit 10 and the radiation detection unit 12 that rotate during the CT imaging from the space of the subject. The breast of the subject, which is held by the breast holding portion 34, is fixed during imaging.

Although the breast holding portion 34 is connected along the periphery of the opening 20 of the front cover 26 in the above example, the breast holding portion 34 may be connected to, for example, the fixed frame 30a of the gantry 30 alternatively.

An inserting portion 24a and an inserting portion 24b are provided in the gantry 30 along the fixed frame 30a of the gantry 30. The operator inserts the hand in the inserting portion 24a and the inserting portion 24b. The inserting portion 24a and the inserting portion 24b are disposed at both side portions of the fixed frame 30a of the gantry 30. The inserting portion 24a and the inserting portion 24b are provided to be line symmetrical about the center line (the dash-dot line) of the gantry 30.

The operator may detach the front cover 26 by inserting the hands in the inserting portion 24a and the inserting portion 24b, and pulling the front cover 26 toward the operator. The operator may access the breast of the subject easily when the front cover 26 during the mammographic imaging is detached.

On the contrary, the operator may attach the front cover 26 to the gantry 30 by pushing in the front cover 26 in the depth direction with respect to the fixed frame 30a of the gantry 30.

The front cover 26 may be opaque from the subject side of the subject of the CT imaging, and may be transparent from the operator side of the mammographic imaging. If the front cover 26 is opaque from the subject side, fear that may be caused by the movement of the radiation generation unit 10 and the radiation detection unit 12 through the front cover 26 is avoidable.

As illustrated in FIGS. 2, 8A, and 8B, a first illumination unit 120 for illuminating the CT imaging side is provided in the front cover 26. For example, the first illumination unit 120 is provided along the circumferential direction of the front cover 26. The first illumination unit 120 may be provided in the gantry 30 (the fixed frame 30a, the elongated cylindrical portion 30b) on the CT imaging side. That is, the first illumination unit 120 is provided so that light is emitted from the breast imaging apparatus 100 on the CT imaging side. It is only required that light is emitted on the front side of the breast imaging apparatus 100 illustrated in FIG. 2. The light emitted from the first illumination unit 120 may be continuous illumination or blinking. Although not illustrated, the illumination unit is controlled by the control unit 110.

During the CT imaging, the control unit 110 makes the first illumination unit 120 emit light. During the CT imaging, light is emitted by the first illumination unit 120 on the CT imaging side. Therefore, the subject of the CT imaging may know which side of the breast imaging apparatus is used for the imaging.

During the CT imaging, the first illumination unit 120 turns off the light emitted on the CT imaging side. During the CT imaging means a period in which the radiation generation unit 10 and the radiation detection unit 12 are rotated and CT imaging is performed. That is, no light is emitted from the first illumination unit 120 during the CT imaging.

A second illumination unit 122 which emits light on the CT imaging side is provided in the radiation generation unit 10. The control unit 110 makes the second illumination unit 122 emit light. Light emitted from the second illumination unit 122 is continuous illumination. Since light emitted from the second illumination unit 122 is continuous illumination, the position of the radiation generation unit 10 or the radiation detection unit 12 may be checked even when the radiation generation unit 10 and the radiation detection unit 12 are rotating.

Since the front cover 26 is translucent, light emitted from the second illumination unit 122 illuminates the CT imaging side. During the CT imaging in which the radiation generation unit 10 and the radiation detection unit 12 are rotating, the radiation generation unit 10 generates radiation and the second illumination unit 122 illuminates light. The operator may check, from the CT imaging side, the positions of the radiation generation unit 10 and the radiation detection unit 12 which are rotating. Therefore, the operator may know how much the radiation generation unit 10 is to be rotated before the CT imaging ends by checking the positions of the radiation generation unit 10 and the radiation detection unit 12 from the CT imaging side. Although the second illumination unit 122 which illuminates light on the CT imaging side is provided in the radiation generation unit 10, the second illumination unit 122 may be provided in the radiation detection unit 12 alternatively.

When the radiation generation unit 10 and the radiation detection unit 12 are rotated and the CT imaging ends, the control unit 110 makes the first illumination unit 120 illuminate light. Light is emitted by the first illumination unit 120 on the CT imaging side. Therefore, the operator and the subject may know that the CT imaging has ended.

As illustrated in FIG. 7, a third illumination unit 124 which illuminates light on the mammographic imaging side is provided in the radiation generation unit 10, the radiation detection unit 12, and the compression plate 14. The third illumination unit 124 may be provided in the gantry 30 (the fixed frame 30a, the elongated cylindrical portion 30b) on the mammographic imaging side. That is, the third illumination unit 124 is provided so that light is emitted from the breast imaging apparatus 100 on the mammographic imaging side. It is only required that light is emitted on the front side of the breast imaging apparatus 100 illustrated in FIG. 7. The light illuminated from the third illumination unit 124 may be continuous illumination or blinking.

During the mammographic imaging, the control unit 110 makes the third illumination unit 124 emit light. During the mammographic imaging, light is emitted by the third illumination unit 124 on the mammographic imaging side. Therefore, the subject of the mammographic imaging may know which side of the breast imaging apparatus 100 is used for the imaging.

Figure 9:
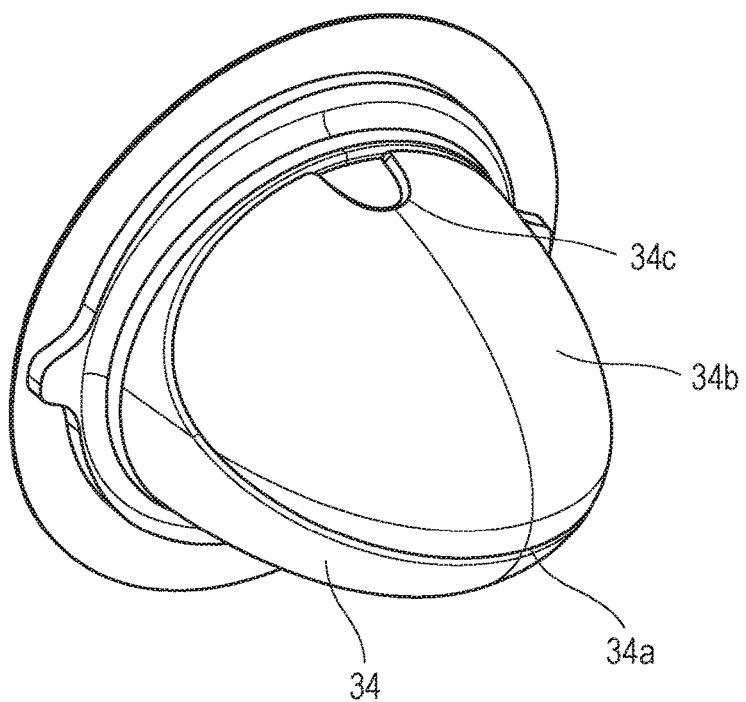
FIG. 9 is a diagram illustrating a state in which a protective cover for protecting the breast is provided in a breast holding portion.

FIG. 9 illustrates a state in which a protective cover 34b for protecting the breast of the subject held by the breast holding portion 34 is provided in the breast holding portion 34.

The breast holding portion 34 has an opening 34a through which the operator accesses the breast from the mammographic imaging side. An upper portion of the breast holding portion 34 is open.

During the CT imaging, the radiation generation unit 10a and the radiation detection unit 12a are rotated when driven by the rotation driving unit 112. Since the breast holding portion 34 is disposed close to the radiation detection unit 12*a*, the radiation detection unit 12*a* passes through the neighborhood of the opening 34*a*. Therefore, if the breast protrudes from the opening 34*a*, the breast held by the breast holding portion 34 can be in contact with the rotating radiation detection unit 12*a*.

Therefore, the breast holding portion 34 is provided with the protective cover 34*b* for protecting the breast in the breast imaging apparatus 100 of the present invention. An outer edge of the opening 34*a* of the breast holding portion 34 conforms to an outer edge of the protective cover 34*b*. The protective cover 34*b* is fit into the breast holding portion 34. The protective cover 34*b* is bowl-shaped similar to the lower part of the breast holding portion 34. The protective cover 34*b* may cover the opening 34*a* of the breast holding portion 34. That is, protrusion of the breast from the opening 34*a* may be avoided by the protective cover 34*b*. Therefore, a possibility of contact between the breast held by the breast holding portion 34 and the rotating radiation detection unit 12*a* is reduced.

The protective cover 34*b* is provided with an inserting portion 34*c* used for the detachment of the protective cover 34*b*. The inserting portion 34*c* is provided at an outer edge of the protective cover 34*b*. The operator inserts the finger in the inserting portion 34*c* to detach the protective cover 34*b*.

The operator may detach the protective cover 34*b* by inserting the finger in the inserting portion 34*c* and pulling the protective cover 34*b* toward the operator. By detaching the protective cover 34*b* before performing the CT imaging, the operator may easily access the breast of the subject of the CT imaging. On the contrary, the operator may attach the protective cover 34*b* by pushing in the protective cover 34 to the opening 34*a* of the breast holding portion 34.

As described above, the front cover 26 for protecting the subject from the radiation generation unit 10 and the radiation detection unit 12 which rotate during the CT imaging is detachably attached to the gantry 30 of the breast imaging apparatus 100 of the present invention. The front cover 26 has the opening 20 in which the breast of the subject is inserted, and the breast holding portion 34 for holding the breast of the subject inserted in the opening 20. The front cover 26 having a function to protect the subject from the radiation generation unit 10 and the radiation detection unit 12 which rotate during the CT imaging, and to hold the breast of the subject is detachably provided in the gantry 30. Therefore, the subject may be protected from the radiation generation unit 10 and the radiation detection unit 12 which rotate during the CT imaging. CT imaging of the breast of the patient while holding the breast suitably is possible.

Support Leg Portion (Recessed Portion)

Figure 10A:
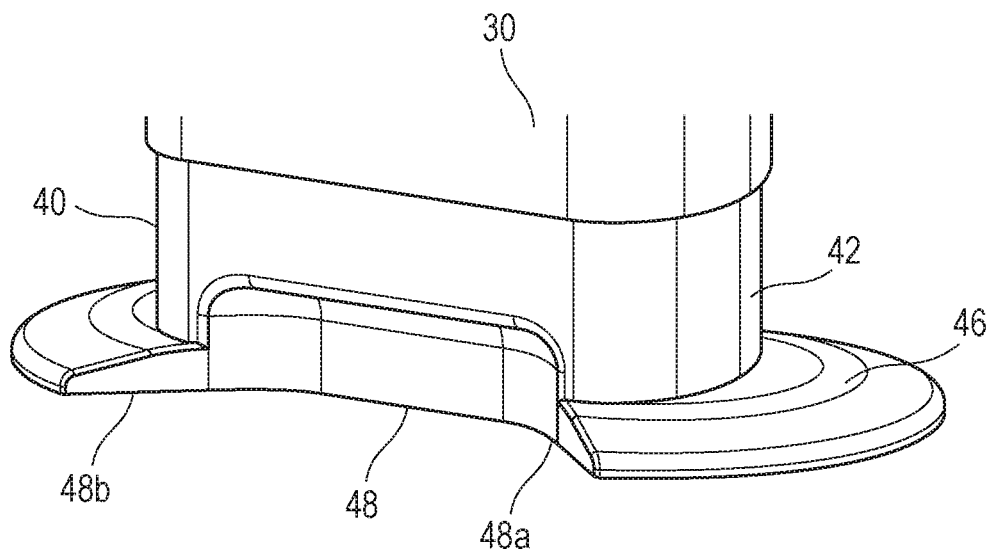
FIGS. 10A and 10B are diagrams illustrating a support leg portion of the breast imaging apparatus of the present invention.
Figure 10B:
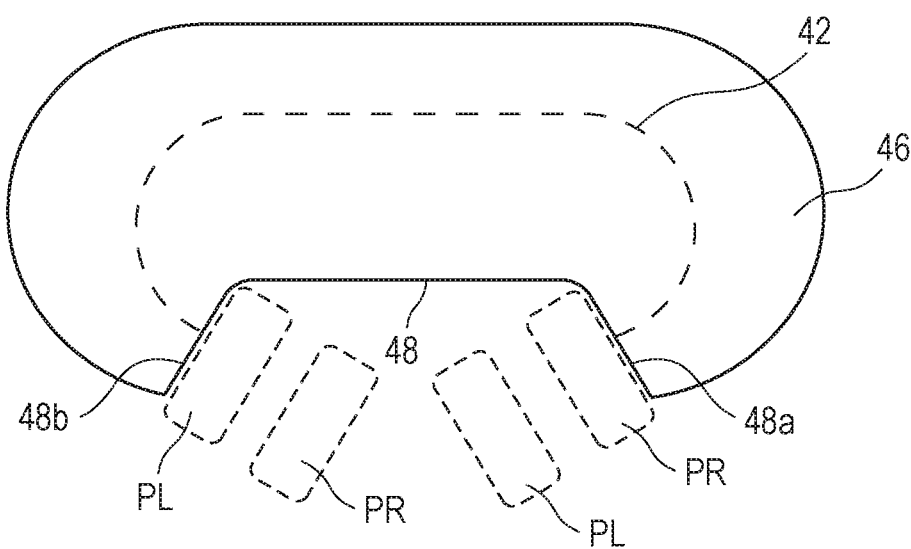

FIGS. 10A and 10B are diagrams illustrating a support leg portion 40 of the breast imaging apparatus 100 of the present invention. As illustrated in FIGS. 2 to 4, 10A and 10B, the breast imaging apparatus 100 is provided with the gantry 30 which supports the imaging unit 102 rotatably, and the support leg portion 40 which supports the breast imaging apparatus 100 (the gantry 30) with respect to the floor. The support leg portion 40 supports the breast imaging apparatus 100 (the gantry 30) vertically.

The support leg portion 40 is constituted by the elongated cylindrical portion 42 extending in the direction crossing perpendicularly the horizontal plane (the vertical direction), and a pedestal portion 46 which is connected to the elongated cylindrical portion 42 for stably supporting the breast imaging apparatus 100 (the gantry 30). The pedestal portion 46 is a member in contact with the floor. The elongated cylindrical portion 42 and the pedestal portion 46 in the support leg portion 40 are integrated with each other. The gantry 30 is connected with the elongated cylindrical portion 42.

The pedestal portion 46 is in contact with the floor. The pedestal portion 46 is formed to conform to the peripheral shape of the elongated cylindrical portion 42. The elongated cylindrical portion 42 has an elongated cylindrical oval shape constituted by two semicircles connected by straight lines. Since the elongated cylindrical portion 42 has an elongated cylindrical oval shape, the pedestal portion 46 is formed in an elongated oval shape. The elongated cylindrical portion 42 and the pedestal portion 46 are similar to each other.

Specifically, the pedestal portion 46 is formed to project outward from the periphery of a bottom surface portion of the elongated cylindrical portion 42. That is, the pedestal portion 46 is formed to uniformly project outward from the periphery of the bottom surface portion of the elongated cylindrical portion 42. The pedestal portion 46 is formed to project outward by a certain width (for example, about 10 to 30 cm) from the periphery of the bottom surface portion of the elongated cylindrical portion 42.

A contact area between the pedestal portion 46 and the floor is larger than an area of the bottom surface portion of the elongated cylindrical portion 42. Since the bottom surface portion of the elongated cylindrical portion 42 is increased by the pedestal portion 46, the breast imaging apparatus 100 may have a greater contact area with the floor. With the pedestal portion 46, an installation balance of the breast imaging apparatus 100 (the gantry 30) may be kept and the breast imaging apparatus 100 (the gantry 30) may be supported stably.

As illustrated in FIGS. 10A and 10B, the support leg portion 40 for supporting the breast imaging apparatus 100 with respect to the floor has the recessed portion 48 in which the subject places the feet. The recessed portion 48 is recessed in shape. FIG. 10A is a diagram illustrating the recessed portion 48 in the support leg portion 40. FIG. 10B is a diagram illustrating the bottom surface portion of the pedestal portion 46, and illustrating a position at which the feet of the subject are placed.

As illustrated in FIGS. 10A and 10B, end portions (tiptoes) of the feet of the subject are placed in the recessed portion 48. The recessed portion 48 opens to a degree to which the end portions (the tiptoes) of the feet of the subject may be placed. Specifically, the recessed portion 48 is formed by detaching a part of the pedestal portion 46 on the predetermined side. That is, the recessed portion 48 has a form in which a hole is formed inside the pedestal portion 46 on the predetermined side. For example, the depth of the recessed portion 48 is about 20 cm and the height of recessed portion 48 is about 10 cm from the floor. The recessed portion 48 may be formed by cutting a part of the elongated cylindrical portion 42 on the predetermined side together with the pedestal portion 46. The predetermined side is the CT imaging side on which the subject is located during the CT imaging. The CT imaging side is the front side in the breast imaging apparatus 100 of FIG. 2, and is the right side in the breast imaging apparatus 100 of FIG. 3.

As illustrated in FIG. 3, during the CT imaging, the breast of the subject is imaged with the radiation generation unit 10 and the radiation detection unit 12 rotated by the rotating frame 38 in a state in which the breast of the subject is inserted in the opening 20 of the front cover 26. During the CT imaging, the subject faces the breast imaging apparatus 100 and the upper body of the subject is in close contact with the front cover 26.

A normal line extending downward from an end surface of the front cover 26 reaches the pedestal portion 46. Therefore, if there is no recessed portion 48 in the pedestal portion 46, the feet of the subject need to be placed on the pedestal portion 46 and the subject needs to take the CT imaging in an unstable posture.

In the breast imaging apparatus 100 of the present invention, the recessed portion 48 in which the subject places the feet is provided. The recessed portion 48 is formed in the pedestal portion 46 to expose the floor. Therefore, when the subject inserts the feet in the recessed portion 48 and places the feet on the floor, the subject may keep the posture while facing the breast imaging apparatus 100. The subject may take the CT imaging in a stable posture.

In consideration of the installation balance of the breast imaging apparatus 100 (the gantry 30), no recessed portion 48 is provided on the side opposite to the predetermined side in the pedestal portion 46. That is, the recessed portion 48 is formed in the support leg portion 40 in a manner such that the installation balance of the breast imaging apparatus 100 (the gantry 30) is not lost.

The pedestal portion 46 protrudes in the similar manner on the CT imaging side as in the mammographic imaging side. The recessed portion 48 in which the feet of the subject are placed is provided in the pedestal portion 46 on the CT imaging side while keeping the position at which the pedestal portion 46 protrudes.

As illustrated in FIG. 10B, when seen the breast imaging apparatus 100 from above, the elongated cylindrical portion 42 and the pedestal portion 46 each have an elongated cylindrical oval shape constituted by two semicircles connected by straight lines with a part cut out. The recessed portion 48 is formed in the elongated cylindrical portion 42 of an elongated cylindrical oval shape by cutting out the straight line portion on the CT imaging side. The recessed portion 48 is formed in the pedestal portion 46 of an elongated cylindrical oval shape by cutting out the straight line portion on the CT imaging side. The semicircular portion of the pedestal portion 46 is not cut out. That is, the recessed portion 48 is formed in a manner such that a peripheral portion (a corner) of the pedestal portion 46 required for the installation balance of the breast imaging apparatus 100 (the gantry 30) remains (the peripheral portion (the corner) of the pedestal portion 46 is kept).

As illustrated in FIG. 10B, the recessed portion 48 is formed to expand from a back end surface of the recessed portion 48. The recessed portion 48 is formed to be line symmetrical. The recessed portion 48 has a substantially trapezoidal shape consisting of two inclined surfaces 48a and 48b when seen the breast imaging apparatus 100 from above. The inclined surfaces 48a and 48b are inclined with respect to the back end surface of the recessed portion 48 and are perpendicular to the floor.

During the CT imaging of the right breast of the subject, the subject stands with the right foot PR in contact with the inclined surface 48a of the recessed portion 48. The subject may take an obliquely right inclined posture to the front cover 26, and may dispose the right breast closer to the front cover 26 compared to the left breast. This causes the subject to easily insert the right breast in the opening 20 of the front cover 26. Therefore, the subject may take CT imaging in a stable posture.

In the same manner, during the CT imaging of the left breast of the subject, the subject stands with the left foot PL in contact with the inclined surface 48b of the recessed portion 48. The subject may take an obliquely left inclined posture to the front cover 26, and may dispose the left breast closer to the front cover 26 compared to the right breast. This causes the subject to easily insert the left breast in the opening 20 of the front cover 26. Therefore, the subject may take CT imaging in a stable posture.

As described above, the recessed portion 48 in which the subject places the feet is provided in the pedestal portion 46 on the CT imaging side. As illustrated in FIGS. 2 to 4, no recessed portion 48 in which the subject places the feet is provided in the pedestal portion 46 on the mammographic imaging side on which the subject is located during the mammographic imaging. That is, the recessed portion 48 is not provided in the support leg portion 40 on the mammographic imaging side. The recessed portion 48 is provided in the support leg portion 40 only on the CT imaging side (the right side). This is because, on the mammographic imaging side, the components of the radiation generation unit 10b, the radiation detection unit 12b, the compression plate 14 and the like protrude on the mammographic imaging side (the left side), i.e., the side of the subject of the mammographic imaging (the left side). The components of the radiation generation unit 10b, the radiation detection unit 12b, the compression plate 14 and the like protrude on the side of the subject of the mammographic imaging (the left side) further than the pedestal portion 46. Therefore, it is not necessary to provide the recessed portion 48 in the pedestal portion 46 on the mammographic imaging side.

As described above, the breast imaging apparatus 100 of the present invention is provided with the support leg portion 40 which supports the gantry 30 with respect to the floor. The support leg portion 40 has the recessed portion 48 in which the subject places the feet.

Imaging is performed with the radiation generation unit 10 and the radiation detection unit 12 rotated in a state in which the part to be imaged of the subject is inserted between the radiation generation unit 10 and the radiation detection unit 12. The recessed portion 48 in which the subject places the feet is formed in the support leg portion 40 on the CT imaging side in which subject is located.

No recessed portion in which the subject places the feet is formed in the support leg portion 40 on the mammographic imaging side on which the subject is located when imaging is performed with the part to be imaged of the subject compressed between the compression plate 14 and the radiation detection unit 12 using the radiation generation unit 10 and the radiation detection unit 12. Therefore, the subject may take a posture suitable for each imaging. Both of the mammographic imaging and the CT imaging while holding the breast of the patient suitably are possible.

Gripping Portion

As illustrated in FIG. 2, a plurality of gripping portions 22a, 22b, 22c, and 22d to be gripped by the subject during the CT imaging are formed in the gantry 30 on the CT imaging side. Specifically, a plurality of gripping portions 22a, 22b, 22c, and 22d are formed along the circumferential direction of an outer edge of the ring-shaped fixed frame 30a which rotatably supports the rotating frame 38 of the gantry 30. A plurality of gripping portions 22a, 22b, 22c, and 22d are formed near the connecting portions of the fixed frame 30a and the front cover 26 provided in the fixed frame 30a.

In the fixed frame 30a, the gripping portion 22a is disposed in the upper right portion, the gripping portion 22b is disposed in the lower right portion, the gripping portion 22c is disposed in the upper left portion, and the gripping portion 22d is disposed in the lower left portion. Although not illustrated, a gripping portion may be disposed in an upper portion in the fixed frame 30a.

A plurality of gripping portions 22a, 22b, 22c, and 22d are formed as recesses, and are formed on the ring-shaped fixed frame 30a. The gripping portion 22 is recessed to such an extent that the fingertip of the subject is caught.

Figure 11:
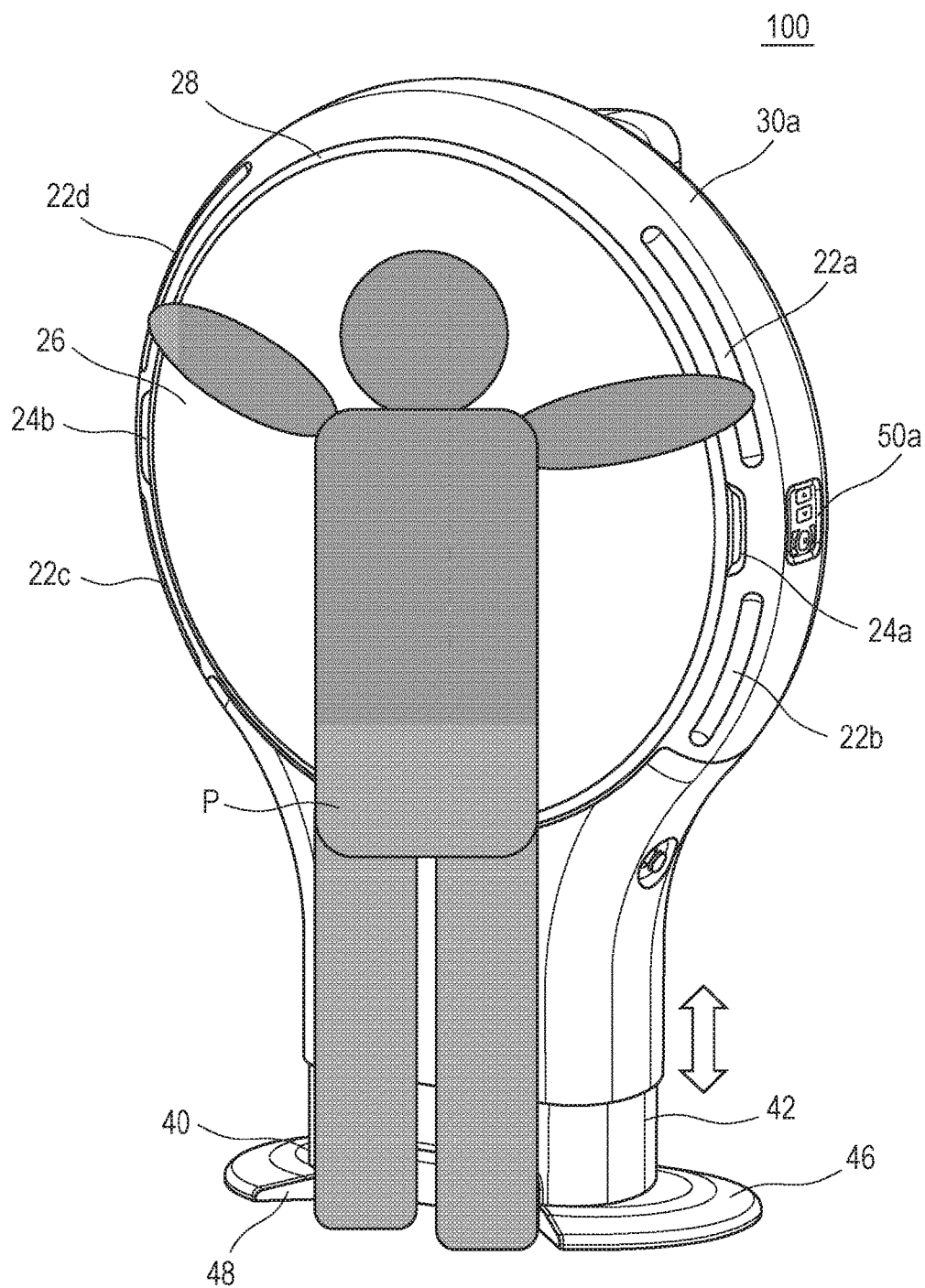
FIG. 11 is a diagram illustrating an imaging form of a subject during the CT imaging.

FIG. 11 is a diagram illustrating an imaging form of a subject P during the CT imaging. The subject P holds at least one of a plurality of gripping portions 22a, 22b, 22c, and 22d. As illustrated in FIG. 11, the subject P may hold the upper gripping portions 22a and 22d of the gantry 30. The end portions (the tiptoes) of the feet of the subject P are placed in the recessed portion 48. The subject P may support the own body by pulling the own body against the gantry 30.

As illustrated in FIG. 4, the gripping portion 70 to be gripped by the subject during the mammographic imaging is provided in the gantry 30 on the mammographic imaging side. The gripping portion 70 is provided along the circumferential direction of the outer edge of the ring-shaped fixed frame 30a. Specifically, the gripping portion 70 is formed to project from two support points in the fixed frame 30a. The support points are located at lower portion in the fixed frame 30a. A distance between the two support points in the gripping portion 70 is longer than the width of the radiation generation unit 10b or the radiation detection unit 12b. The distance between the two support points in the gripping portion 70 is longer than the width of the support base 2.

The gripping portion 70, which is a bar-shaped member, is disposed to arch between the two support points in the fixed frame 30a. The gripping portion 70 is a handrail-like member. The gripping portion 70 is curved. Specifically, the gripping portion 70 is curved downward. This is to prevent the radiation generation unit 10 and the radiation detection unit 12 from interfering (colliding) with the gripping portion 70 during rotation of the radiation generation unit 10 and the radiation detection unit 12.

There is a gap between the fixed frame 30a and the arched portion of the gripping portion 70. The gap is about several centimeters. Since there is a gap between the fixed frame 30a and the arched portion of the gripping portion 70, the subject may hold the gripping portion 70 with both hands.

Figure 12:
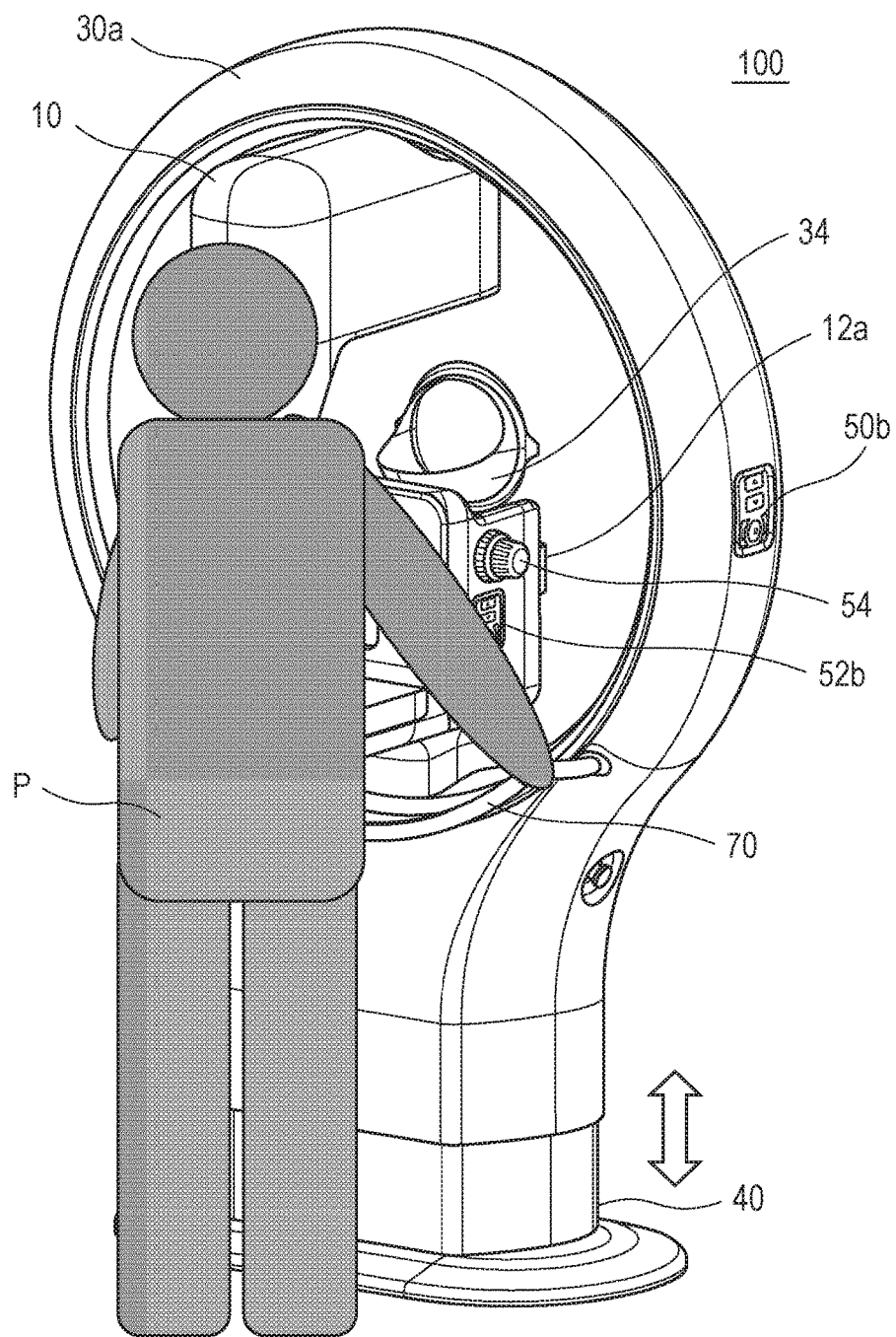
FIG. 12 is a diagram illustrating an imaging form of a subject during the mammographic imaging.

FIG. 12 is a diagram illustrating an imaging form of the subject P during the mammographic imaging. The subject P holds the gripping portions 70 with both hands. The subject P may support the own body by pulling the own body against the gantry 30.

Since the distance between the two support points in the gripping portion 70 is longer than the width of the radiation generation unit 10b or the radiation detection unit 12b, the gripping portion 70 is not located behind the radiation generation unit 10 and the radiation detection unit 12 when the radiation generation unit 10 and the radiation detection unit 12 rotate. The subject may hold the gripping portion 70 when the radiation generation unit 10 and the radiation detection unit 12 rotate.

A plurality of gripping portions 22a, 22b, 22c, and 22d on the CT imaging side differ from the gripping portion 70 on the mammographic imaging side in shape. The gripping portions 22a, 22b, 22c, and 22d on the CT imaging side are formed to recess with respect to the gantry 30, whereas the gripping portion 70 on the mammographic imaging side is formed to project with respect to the gantry 30.

On the CT imaging side, the subject needs to closely press the upper body against the front cover 26 and insert the breast which is the part to be imaged in the opening 20. Therefore, the gripping portions 22a, 22b, 22c, and 22d on the CT imaging side are formed not to project from the gantry 30 to prevent interference with the subject who is in close contact with the front cover 26. The gripping portions 22a, 22b, 22c, and 22d on the CT imaging side are formed as recesses.

The subject does not closely press the upper body against the front cover 26 on the mammographic imaging side. It is necessary to insert the breast of the subject between the compression plate 14 and the radiation detection unit 12 projecting from the gantry 30, and then compress the breast. It is also necessary to support the body of the subject with the breast of the subject compressed. The gripping portion 70 on the mammographic imaging side projects from the gantry 30. The gripping portion 70 on the mammographic imaging side is formed as a projecting form.

As described above, the first gripping portion 70 to be held by the subject is provided in the gantry 30 on the first side of the breast imaging apparatus 100 of the present invention, and the second gripping portion 22 which differs from the first gripping portion 70 in shape is provided in the gantry 30 of the second side opposite to the first side. The first gripping portion 70 is formed to project from the gantry 30 and the second gripping portion 22 is formed as a recess on the gantry 30.

Therefore, the subject of the mammographic imaging and the subject of the CT imaging may take a posture suitable for imaging by holding the first gripping portion 70 and the second gripping portion 22, respectively. Both of the mammographic imaging and the CT imaging while holding the breast of the patient suitably are possible.

Manipulation Unit

As illustrated in FIGS. 2 and 4, the manipulation unit 50 with which the operator manipulates the breast imaging apparatus 100 is provided in the gantry 30. The manipulation unit 50 is provided in an unrotating component in the breast imaging apparatus 100. The manipulation unit 50 is provided on both side surfaces of the fixed frame 30a in the gantry 30. Specifically, the manipulation unit 50 consists of a manipulation unit 50a and a manipulation unit 50b. The manipulation unit 50a is provided at the right end and the manipulation unit 50b is provided at the left end of the fixed frame 30a. As illustrated in FIG. 5, the manipulation unit 50 (the manipulation unit 50a and the manipulation unit 50b) is connected to the control unit 110.

As illustrated in FIG. 4, the manipulation unit 52 (a manipulation unit 52a and a manipulation unit 52b) with which the operator manipulates the breast imaging apparatus 100 is disposed in the support base 2 provided in the rotating frame 38. That is, the manipulation unit 52 is provided in a rotating component in the breast imaging apparatus 100. In the present embodiment, the manipulation unit 52 is provided on both side surfaces of the support base 2. Specifically, the manipulation unit 52 consists of a manipulation unit 52a and a manipulation unit 52b. The manipulation unit 52a and the manipulation unit 52b are provided on both side surfaces of the support base 2. As illustrated in FIG. 5, the manipulation unit 52 (the manipulation unit 52a and the manipulation unit 52b) is connected to the control unit 110.

The manipulation unit 50 provided in the gantry 30 and the manipulation unit 52 provided in the support base 2 are the same in button configuration. The manipulation unit 50 and the manipulation unit 52 are the same in function. The manipulation unit 50 and the manipulation unit 52 each consist of a button for moving the compression plate 14 up and down, and a button for rotating the radiation generation unit 10 and the radiation detection unit 12. The operator presses these buttons with the finger.

Figure 13:
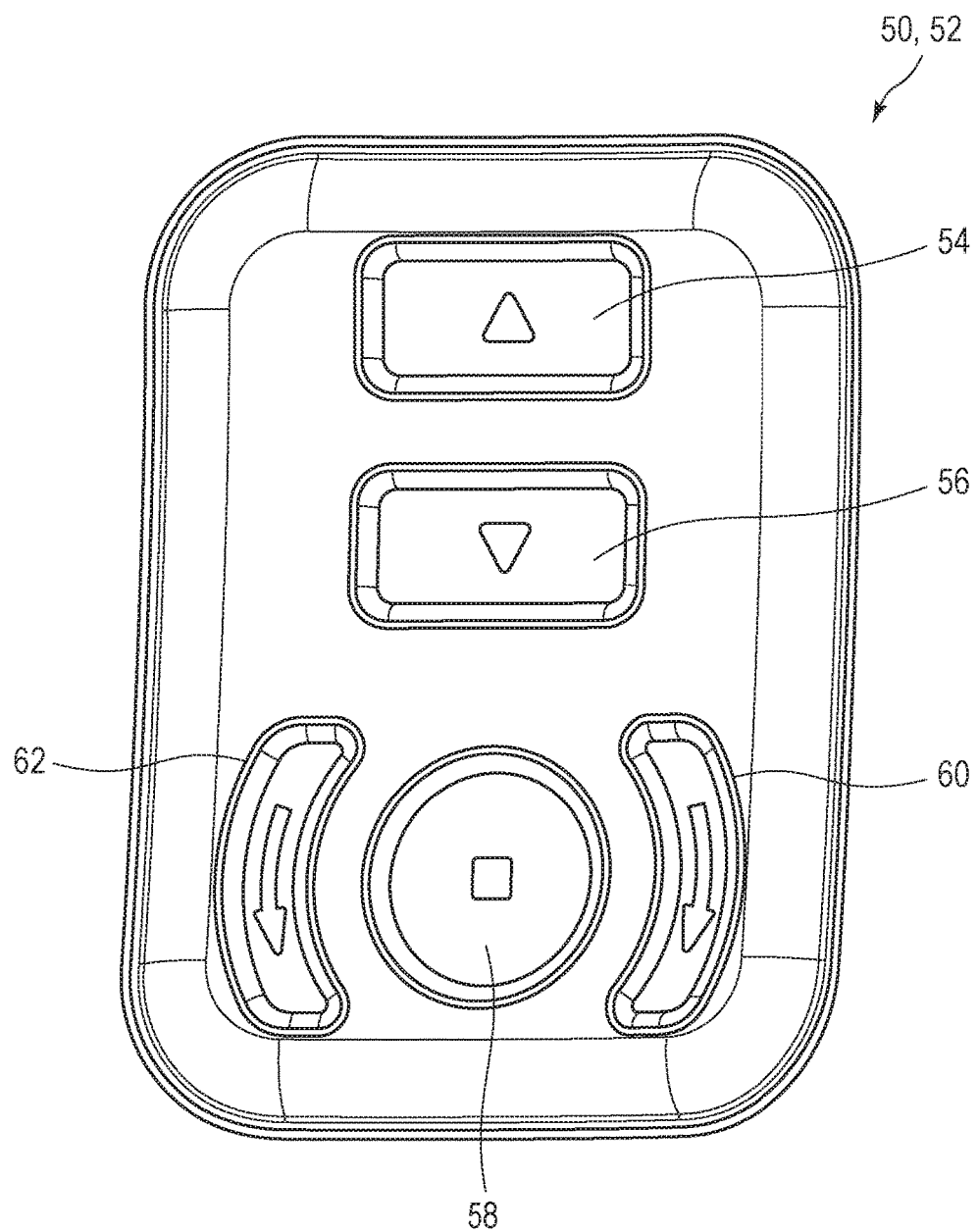
FIG. 13 is a diagram illustrating a button configuration of a manipulation unit of the breast imaging apparatus of the present invention.

FIG. 13 is a diagram illustrating button configurations of the manipulation unit 50 and the manipulation unit 52. Specifically, the manipulation unit 50 and the manipulation unit 52 are constituted by an up button 54, a down button 56, a home position button 58, a clockwise rotation button 60 and a counterclockwise rotation button 62. Each of the buttons is connected to the control unit 110 for various kinds of control. The manipulation unit 50 and the manipulation unit 52 are used mainly for the mammographic imaging.

The up button 54 is used to move the compression plate 14 upward (toward the radiation generation unit 10). The down button 56 is used to move the compression plate 14 downward (toward the radiation detection unit 12).

The clockwise rotation button 60 is used to rotate the rotating frame 38 clockwise in order to rotate the radiation generation unit 10 and the radiation detection unit 12 clockwise. The counterclockwise rotation button 62 is used to rotate the rotating frame 38 counterclockwise in order to rotate the radiation generation unit 10 and the radiation detection unit 12 counterclockwise.

When the operator presses the clockwise rotation button 60, the control unit 110 makes the radiation generation unit 10 and the radiation detection unit 12 rotate clockwise using the rotation driving unit 112. Specifically, when the operator presses the clockwise rotation button 60 once, the control unit 110 makes the radiation generation unit 10 and the radiation detection unit 12 rotate clockwise once. The positions of the radiation generation unit 10 and the radiation detection unit 12 before rotation and the positions of the radiation generation unit 10 and the radiation detection unit 12 after rotation are the same.

When the operator holds down the clockwise rotation button 60, the control unit 110 makes the radiation generation unit 10 and the radiation detection unit 12 rotate clockwise at a low speed using the rotation driving unit 112. The rotational speed of the radiation generation unit 10 and the radiation detection unit 12 when the clockwise rotation button 60 is held down is lower than the rotational speed at which the radiation generation unit 10 and the radiation detection unit 12 are rotated once and the rotational speed during the CT imaging. When the operator releases the clockwise rotation button 60, the control unit 110 stops the radiation generation unit 10 and the radiation detection unit 12 at that positions, and rotation of the radiation generation unit 10 and the radiation detection unit 12 stops.

Similarly, when the operator presses the counterclockwise rotation button 62, the control unit 110 makes the radiation generation unit 10 and the radiation detection unit 12 rotate counterclockwise using the rotation driving unit 112. Specifically, when the operator presses the counterclockwise rotation button 62 once, the control unit 110 makes the radiation generation unit 10 and the radiation detection unit 12 rotate counterclockwise once. The positions of the radiation generation unit 10 and the radiation detection unit 12 before rotation and the positions of the radiation generation unit 10 and the radiation detection unit 12 after rotation are the same.

When the operator holds down the counterclockwise rotation button 62, the control unit 110 makes the radiation generation unit 10 and the radiation detection unit 12 rotate counterclockwise at a low speed using the rotation driving unit 112. When the operator releases the counterclockwise rotation button 62, the control unit 110 stops the radiation generation unit 10 and the radiation detection unit 12 at that positions, and rotation of the radiation generation unit 10 and the radiation detection unit 12 stops.

Holding down of the clockwise rotation button 60 or the counterclockwise rotation button 62 is ideal for the angle setting of the radiation generation unit 10 and the radiation detection unit 12 during the mammographic imaging (MLO).

The home position button 58 is used to rotate the radiation generation unit 10 and the radiation detection unit 12 clockwise or counterclockwise to move the radiation generation unit 10 up and move the radiation detection unit 12 down as illustrated in FIG. 4. At the home position, the radiation generation unit 10 has been moved to the upper position and the radiation detection unit 12 has been moved to the lower position, and the radiation generation unit 10 and the radiation detection unit 12 are arranged in the direction of the normal line. The home position state is the CC view state in the mammographic imaging.

When the home position button 58 is pressed, even if the radiation generation unit 10 and the radiation detection unit 12 are inclined, the control unit 110 makes the radiation generation unit 10 and the radiation detection unit 12 rotate using the rotation driving unit 112 to the home position. The control unit 110 makes the radiation generation unit 10 and the radiation detection unit 12 rotate clockwise or counterclockwise at a low speed. The rotational speed of the rotation to the home position is lower than the rotational speed at which the radiation generation unit 10 and the radiation detection unit 12 are rotated once and the rotational speed at which the radiation generation unit 10 and the radiation detection unit 12 are rotated during the CT imaging.

The manipulation unit 50 may have a gantry up-and-down button used to move the gantry 30 up and down. When the gantry up-and-down button is pressed, the control unit 110 may move the gantry 30 up and down using the up/down driving unit described above. The height of the gantry 30 may be adjusted in accordance with the height of the subject.

As described above, the first manipulation unit 50 with which the operator manipulates the breast imaging apparatus 100 is provided in the gantry 30 of the breast imaging apparatus 100 of the present invention, and the second manipulation unit 52 having the same function as that of the first manipulation unit 50 is provided in the support base 2 supporting the radiation detection unit 12.

Therefore, the operator may manipulate the breast imaging apparatus 100 with the manipulation unit in accordance with the imaging form of the subject.

Console

Figure 14:
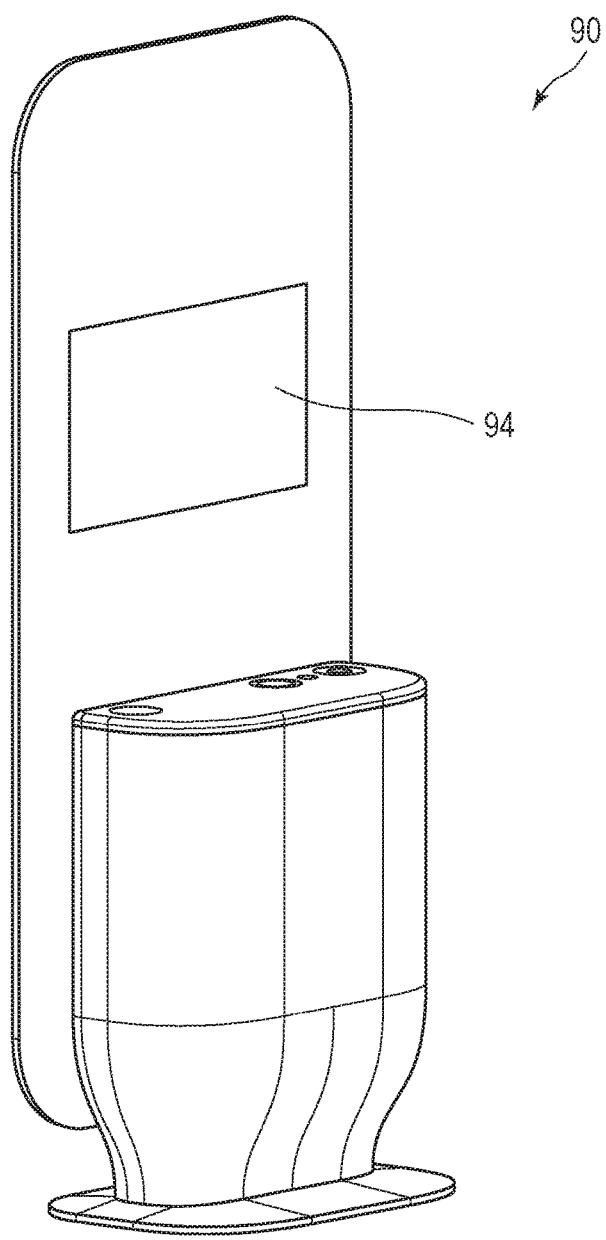
FIG. 14 is a diagram illustrating a console of the breast imaging apparatus of the present invention.

FIG. 14 is a diagram illustrating the console 90 manipulated by the operator. The console 90 is provided outside an imaging room. The console 90 consists of a button for moving the compression plate 14 up and down, and a button for rotating the radiation generation unit 10 and the radiation detection unit 12 as in the case of the manipulation units 50 and 52. The console 90 is connected to the control unit 110 as illustrated in FIG. 5.

The console 90 differs from the manipulation units 50 and 52 in that the console 90 is provided with a button regarding CT imaging and a display unit 94. The manipulation units 50 and 52 are each provided with a button regarding mammographic imaging, whereas the console 90 is provided with a button regarding mammographic imaging and a button regarding CT imaging.

When the operator presses the button regarding the CT imaging provided in the console 90, the control unit 110 may perform CT imaging with the radiation generation unit 10 and the radiation detection unit 12 rotating.

As described above, the breast imaging apparatus 100 may perform mammographic imaging with the breast of the subject compressed between the compression plate 14 and the radiation detection unit 12. The control unit 110 of the breast imaging apparatus 100 generates a mammogram image based on the imaged radiation data. The display unit 94 in the console 90 displays the generated mammogram image.

The breast imaging apparatus 100 may perform CT imaging with the radiation generation unit 10 and the radiation detection unit 12 rotating. The control unit of the breast imaging apparatus 100 may generate a CT image by reconstructing the imaged radiation data. The display unit 94 in the console 90 displays the generated CT image.

An example in which the breast imaging apparatus 100 of the present invention is provided with two sets of radiation generation units and radiation detection units for the CT imaging and for the mammographic imaging is described. Alternatively, it is also possible to implement CT imaging and mammographic imaging using one set of radiation generation unit and radiation detection unit. Specifically, the breast imaging apparatus 100 is provided with a moving mechanism (not illustrated) for moving the radiation generation unit and the radiation detection unit depending on CT imaging and mammographic imaging. During the CT imaging, for example, the radiation generation unit is moved to the position of 10a and the radiation detection unit is moved to the position of 12a illustrated in FIG. 3. During the mammographic imaging, the radiation generation unit is moved to the position of 10b and radiation detection unit is moved to the position of 12b illustrated in FIG. 3.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-132185, filed Jun. 30, 2015, which is hereby incorporated by reference herein in its entirety.

What is claimed is:

1. A breast imaging apparatus, comprising a gantry which includes a generation unit configured to generate an x-ray radiation and a detection unit configured to detect the x-ray radiation generated by the generation unit, the generation unit and the detection unit being capable of rotating facing each other, wherein the gantry is provided with a front cover configured to protect a subject from the generation unit and the detection unit which rotate during CT imaging, and the front cover has an opening in which the breast of the subject is inserted and a breast holding portion configured to hold the breast of the subject inserted in the opening, and wherein the front cover is detached from the gantry during mammographic imaging in which the breast of the subject is compressed between a compression plate and the detection unit and imaged with the x-ray radiation.

2. The breast imaging apparatus according to claim 1, wherein the gantry includes a rotating frame configured to rotate the generation unit and the detection unit facing each other, and a fixed frame configured to support the rotating frame rotatably, and the fixed frame is attached to the front cover.

3. The breast imaging apparatus according to claim 2, wherein the front cover is round shaped and has an opening at the center thereof in which the breast of the subject is inserted.

4. The breast imaging apparatus according to claim 1, wherein the front cover is formed of a radiation-shielding member.

5. The breast imaging apparatus according to claim 1, wherein the front cover is formed of a translucent member.

6. The breast imaging apparatus according to claim 1, wherein the breast holding portion is formed along the periphery of the opening.

7. The breast imaging apparatus according to claim 1, wherein the breast holding portion is formed of a transparent, radiation-transmissive member.

8. The breast imaging apparatus according to claim 1, wherein the breast holding portion is hollow and is curved to conform to the shape of the breast of the subject.

9. The breast imaging apparatus according to claim 1, wherein the breast holding portion is partly open.

10. The breast imaging apparatus according to claim 9, wherein a protective cover configured to protect the breast of the subject held by the breast holding portion is provided in the breast holding portion.

11. The breast imaging apparatus according to claim 1, wherein the breast holding portion is attachable to and detachable from the front cover.

12. The breast imaging apparatus according to claim 1, wherein a first illumination unit configured to illuminate a CT imaging side is provided in the front cover.

13. The breast imaging apparatus according to claim 1, wherein a first illumination unit configured to illuminate a CT imaging side is provided in the generation unit.

* * * * *